United States Patent
Hendrick, III et al.

(10) Patent No.: US 9,875,450 B1
(45) Date of Patent: Jan. 23, 2018

(54) SYSTEM AND METHOD OF AUTOMATED HEALTHCARE ASSESSMENTS AND EVENT INFERENCES

(71) Applicants: James Robert Hendrick, III, Nashville, TN (US); Jonathan Eddy Barnes, Nashville, TN (US); Andrew Thomas Johnson, Franklin, TN (US); James E. Anderson, III, Nashville, TN (US); Christopher Paul McIntyre, Nashville, TN (US)

(72) Inventors: James Robert Hendrick, III, Nashville, TN (US); Jonathan Eddy Barnes, Nashville, TN (US); Andrew Thomas Johnson, Franklin, TN (US); James E. Anderson, III, Nashville, TN (US); Christopher Paul McIntyre, Nashville, TN (US)

(*) Notice: Subject to any disclaimer, the term of this patent is extended or adjusted under 35 U.S.C. 154(b) by 652 days.

(21) Appl. No.: 14/013,132

(22) Filed: Aug. 29, 2013

Related U.S. Application Data

(60) Provisional application No. 61/694,532, filed on Aug. 29, 2012.

(51) Int. Cl.
  *G06Q 50/22* (2012.01)
  *G06Q 50/24* (2012.01)
  (Continued)

(52) U.S. Cl.
  CPC ..... *G06Q 10/0631* (2013.01); *G06F 19/3431* (2013.01); *G06Q 50/22* (2013.01)

(58) Field of Classification Search
  CPC ............. G06F 19/3418; G06F 19/3481; G06F 19/3406; G06C 50/24; G06Q 50/22; G06Q 10/06; G06Q 10/10; G06Q 50/24
  See application file for complete search history.

(56) References Cited

U.S. PATENT DOCUMENTS 5,544,649 A   8/1996  David et al.
6,611,206 B2  8/2003  Eshelman et al.
(Continued)

FOREIGN PATENT DOCUMENTS

WO    2007079154    12/2007

OTHER PUBLICATIONS

Druker, David: Innovation Center, California, Druker Center of Health Systems Innovation, "Announcing the Winners of the link-Ages Kickoff Weekend Developer" (Apr. 24, 2012).

*Primary Examiner* — Maroun Kanaan
(74) *Attorney, Agent, or Firm* — Patterson Intellectual Property Law, P.C.; Gary L. Montle

(57) ABSTRACT

A healthcare assessment system is provided for a plurality of healthcare facilities each having healthcare providers and residential areas, each area equipped with biometric sensors and activity sensors. A central server receives sensor data and stores subject information in a data storage network. The system determines potential events for each subject based on respective healthcare profiles, and an event inference engine identifies the actual occurrence and extrapolates a likely occurrence of potential events based on the stored data points with respect to time. The system assigns values representative of a level of healthcare resource needs for each subject, and values representative of a quality of healthcare resources provided for each healthcare provider. A graphical user interface includes a resource allocation report with user-selectable lists of relative rankings of the assigned values for each subject and each provider in a healthcare facility, or for each respective healthcare facility.

19 Claims, 14 Drawing Sheets

(51) Int. Cl.
*G06Q 10/06* (2012.01)
*G06F 19/00* (2011.01)

(56) References Cited

U.S. PATENT DOCUMENTS

| | | |
|---|---|---|
| 7,733,224 B2 | 6/2010 | Tran |
| 7,917,376 B2 | 3/2011 | Bellin et al. |
| 2003/0181790 A1 | 9/2003 | David et al. |
| 2003/0208109 A1 | 11/2003 | David et al. |
| 2004/0019515 A1* | 1/2004 | Senyurt ............ G06Q 10/06311 |
| | | 705/7.13 |
| 2008/0001735 A1* | 1/2008 | Tran .................... G06F 19/3418 |
| | | 340/539.22 |
| 2010/0145164 A1 | 6/2010 | Howell |
| 2013/0173294 A1* | 7/2013 | Hyde .................... G06Q 50/24 |
| | | 705/3 |

* cited by examiner

Logged in as Jim Anderson (Log Out)

Dashboard | Reminders | Activity | Medical | Options | Help

◯ Care Technology Systems

Care Notes
New Note

Jim Anderson 05/04/2011 07:31 PM Edit Delete
Needs help getting a light bulb changed if anyone has the time to stop by.

Jim Anderson 05/04/2011 07:30 PM Edit Delete
Mom's having a great day today and went on a short walk. Her left ankle is a little sore, though.

Jim Anderson 05/04/2011 07:29 PM Edit Delete
Mom has been a little down due to all the rain and has "cabin fever." I think she'd appreciate a phone call or two.

Andrew Johnson 04/25/2011 11:25 AM Edit Delete

Alerts

05/01/2011 08:36 AM
Carolyn got out of bed

05/01/2011 07:37 AM
Refrigerator Door has been opened 10 times in the last 12 hours.

05/01/2011 04:57 AM
The front door was opened between the hours of 12:00AM and 6:00AM

Carolyn Anderson
Edit Carolyn's Profile

Address: Street Address here
City, State  Zip here

Home Phone: (XXX) XXX-XXXX
Cell Phone: (XXX) XXX-XXXX

Primary Family or Friend
Jim Anderson
Details

Formal Caregiver
Andrew Johnson
Details

Recent Activity

Most Recent Activity:
Bed Pressure on 05/04/2011 at 10:45 PM

Last Time in Bed:
06/04/2011 at 10:45 PM

Last Time Out of Bed:
06/04/2011 at 08:32 AM

Sensor Activity Per Room

Rooms
▨ Living Room   ▤ Bed
▨ Entryway     □ Bathroom
   Kitchen

SYSTEM AND METHOD OF AUTOMATED HEALTHCARE ASSESSMENTS AND EVENT INFERENCES

CROSS-REFERENCES TO RELATED APPLICATIONS

This application claims benefit of the following patent application(s) which is/are hereby incorporated by reference: U.S. Provisional Patent Application No. 61/694,532, filed Aug. 29, 2012.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present disclosure pertains to systems, methods and readable medium providing remote monitoring services for people at risk for health conditions and communication of potential emergent health situations to third parties.

Health conditions including the onset of old age often present situations in which patients are unable to provide for their own care. These patients are considered "at risk" and as such often require supervision (monitoring) on a consistent and/or ongoing basis. At risk persons may be prone to certain emergent events such as stroke, coronary events, falls, etc. They may also be suffering from decreased mental capacity, frailty and/or the effects of aging.

The benefits of a patient being able to recuperate and/or age in familiar surroundings are well-documented. That is just one of the many advantages of remaining in the home including the financial advantage when compared to cost of a long-term care facility or other medical facility.

Today, remote monitoring systems are widely used in the home security industry as well as in patient monitoring applications. Remote Monitoring Systems typically consists of sensors and a central control device (i.e. PCB). When a sensor is tripped, a communication is initiated (i.e. via phone line, cell, etc.) to a central monitoring source (i.e. call center) that can provided automated response and/or live response to assess and address an emergent situation. Sensors for home security systems typically include motion detectors, door contacts, smoke detectors, flood detectors and/or video cameras. Patient monitoring systems may also include bed/chair pressure pads as well as personal emergency response systems (i.e. panic buttons).

To better control the cost of healthcare services, many providers and insurers are using electronic and automated technologies to minimize the amount of human resources required to deliver services. This is true of the remote monitoring services of at risk patients as well. Manual monitoring by human supervision is costly, subject to human error and often inconsistent across multiple caregivers.

Yet according to the AARP, 89% of seniors prefer to remain living independently in their homes as they age. As is widely noted, the baby boomers are entering into the ranks of senior citizens, and the need for solutions that will allow them to do so and remain in their homes safely is clear.

For patients seeking to remain living independently, self-monitoring is one option. Self-monitoring solutions require a patient to request assistance with a panic button or comparable one-touch emergency response technology. These systems have proven to be less than sufficient for various reasons. Non-compliance (i.e. failure to wear the device) is a primary cause. In addition, studies have shown that as much as 50% of patients who experience a fall or other medical condition while wearing the device are disoriented or otherwise incapacitated to the point that they do not utilize the device.

Another option to remain living independently is to utilize layperson and/or professional caregivers. If the patient has family members and/or friends they may act in the role of informal caregiver and monitor the patient. However, they are often unable to cover the full 24-hour period, and/or are obligated otherwise (i.e. a career commitment) and/or are not familiar with the needs of the task and/or otherwise unable to fulfill the monitoring duties. There also exist questions regarding continuity and consistency of the monitoring.

Professional caregivers may also provide care in conjunction with or independent of informal caregivers. Professional caregivers, both skilled (i.e. nurses) and non-skilled (household taskmasters), come at an expense. These services may be provided on a less than 24 hour basis. However, sufficient coverage by caregivers may not be possible either due to financial constraints and/or the preference of the patient and/or caregivers. Additionally, the caregiver or a group of caregivers may not be able to provide a complete, accurate and consistent monitoring.

Remote collection of biometric data to assess and/or monitor the condition of at risk patient has emerged as a widely accepted alternative to keeping a patient in a hospital-stay observation. Many early versions of remote biometric monitoring utilized data collection devices at the source that would record over a period of time and then be returned in order for the data to be extracted and analyzed. Those systems evolved with the proliferation of communication technologies (i.e. internet, cellular, 3G, etc.) that no longer required physical access to the recording device in order to access the data.

Economies of scale and technology allowed more cost effective monitoring devices to be developed. The proliferation of internet, cellular and other digital communications continues to reduce the cost of monitoring at risk patients long term or even in perpetuity. These systems also evolved to more offer real-time data analysis and event monitoring.

Many biometric devices as are currently known in the art (e.g. weight scales, glucose meters, pulse/oximeters and blood pressure) are effective when in use but are unable to capture activities of daily living which can be indicative of an emergent condition.

Similar to biometric monitoring, remote security systems as are currently known in the art (motion detectors, door contacts, pressure pads, flood detectors, etc.) have found comparable economies of scale and have benefited from the proliferation of communications options.

Remote monitoring systems have the ability to capture lifestyle activity, and both systems are focused on protecting the well-being of the individual utilizing them. When combined, these systems are better able to determine a cause and effect relationship between lifestyle and a health-threatening event, and provide more comprehensive monitoring for the patient.

Thus, there is a need for a product that combines biometric data reporting and lifestyle data in order to provide a more complete approach to remote patient monitoring.

More particularly, there is a need for a system that allows a patient to continue to live independently while providing comprehensive (24 hour) monitoring, alerting caregivers to emergent situations, and providing analytical reporting to enable quality care of at risk patients.

This need is particularly relevant in the context of falls, as alluded to previously. According to the CDC in 2010, over fifty percent of falls among seniors were never reported to a health professional. This is attributed to several different factors including but not limited to the embarrassment of the senior, the senior being unaware of the implications and importance of reporting the fall, and concern that knowledge of the fall may lead relatives and/or health professionals to change the seniors living conditions. However, previous falls are a strong indicator of the potential for future falls. In fact, fall scores (the number of previously recorded falls) are used as best practice as a quantifiable method for determining certificate of need for senior care. Based on 2010 U.S. Census data, 1.5% of seniors (age 65 and older) will have a fall that requires hospitalization. With over 40 million seniors in 2010, the average cost of a fall requiring hospitalization was $17,500, making this an estimated $10 billion annual healthcare expenditure. The trend of an increasingly larger population over the age of 65 and rising costs in healthcare has led healthcare providers and health plans to seek technology solutions to help maintain a healthy population and control healthcare costs.

Therefore, there is further a need for a low cost and non-obtrusive technology solution for predicting falls before they occur to keep seniors healthier, allow those seniors to remain in their homes longer, and help both seniors and health plans avoid downstream costs.

BRIEF SUMMARY OF THE INVENTION

A healthcare assessment system in accordance with an embodiment of the present disclosure is provided for a plurality of residential areas in a healthcare facility, each area associated with a healthcare subject and further including a first set of one or more sensors effective to generate output signals representative of biometric data for the subject, and a second set of one or more sensors effective to generate output signals representative of activity by the subject. A centralized server is functionally linked via a communications network to the sensors and directs the performance of a method of the present disclosure. Biometric and activity data points for each subject are stored in a data storage network, and the system determines potential events relevant to each subject for system monitoring based on a respective healthcare profile. An event inference engine identifies the actual occurrence and extrapolates likely occurrence of one or more potential events based on one or more stored data points with respect to time, and the system assigns values representative of a level of healthcare resource needs for each subject, the values determined based on respective healthcare profiles and the identified and extrapolated events.

In one further aspect of a system as disclosed herein, a graphical user interface is generated on a display unit of a user computing device, which includes a resource allocation report with relative rankings of the assigned values for each subject associated with the healthcare facility.

In another aspect, an operation of extrapolating the likely occurrence of potential events involves matching an identified combination of data points with a predetermined combination of data points representative of an event relevant to a high-risk condition associated with the respective subject.

In another aspect, the method includes categorizing the identified or extrapolated events as billable events with respect to a particular subject, and may further include cross-checking the categorized billable events against a list of actual billed events with respect to the subject. A second user interface may be provided to enable user confirmation of one or more categorized billable events with respect to the subject.

In another aspect, the resource allocation report may further include a graphical event log display with one or more primary data points corresponding to an event definition, and one or more secondary data points retroactively defined as relevant in view of an extrapolated event occurrence. A first time range is highlighted between at least first and second primary data points corresponding to an event period, and one or more time ranges are separately highlighted between secondary and a primary data points on either end of the event period.

In one embodiment of a system according to the present disclosure, scores are further generated for each of a plurality of healthcare providers in a given facility, wherein program engines generate relative rankings for the providers alongside those of the associated subjects. Resource allocation engines may subsequently report the relative rankings for the subjects and providers, collectively or according to user selection, with respect to a given healthcare facility. The resource allocation engines may further generate recommendations for resource allocation based on the relative rankings of the subjects and healthcare providers, and further in addition to for example the subject healthcare profiles.

In one embodiment of a system according to the present disclosure, relative rankings and resource allocation recommendations may further be generated for each of a plurality of healthcare facilities in accordance with scores for associated subjects and healthcare providers. Resource allocation reports may be generated with relative rankings according to user selection of any one or more of subjects for a particular facility, providers for a particular facility, or more generally across a number of facilities.

In various embodiments, a host system in accordance with the present disclosure may generally be able to make information available about a subject and distribute that information via internet, phone, text, tweet, smart watch (i.e. Pebble), etc. The system may issue alerts that prompt for intervention via, e-mail, text, tweet, phone call, smart watch (i.e. Pebble) or other communication means. The system may generate a newsletter of aggregate and/or select information from the data set(s), automate social network postings, and serve as an addendum to care record and/or EHRs (Electronic Health Records).

Generally stated, a host system and associated methods of the present disclosure may further enable remote monitoring systems over 3G machine to machine (M2M) networks with one-way and two-way communication, enable smart remote monitoring, enable a passive data collection mechanism, enable and enhance feedback to and among senior caregivers, identify and notify caregivers to health-related events, identify symptomatic indicators and predict health-related threats, and provide quantifiable triggers and/or alerts for intervention.

BRIEF DESCRIPTION OF THE SEVERAL VIEWS OF THE DRAWINGS

FIG. 9 is an image representing a screen shot from an exemplary user interface generated by a system according to the present disclosure.

DETAILED DESCRIPTION OF THE INVENTION

Figure 1:
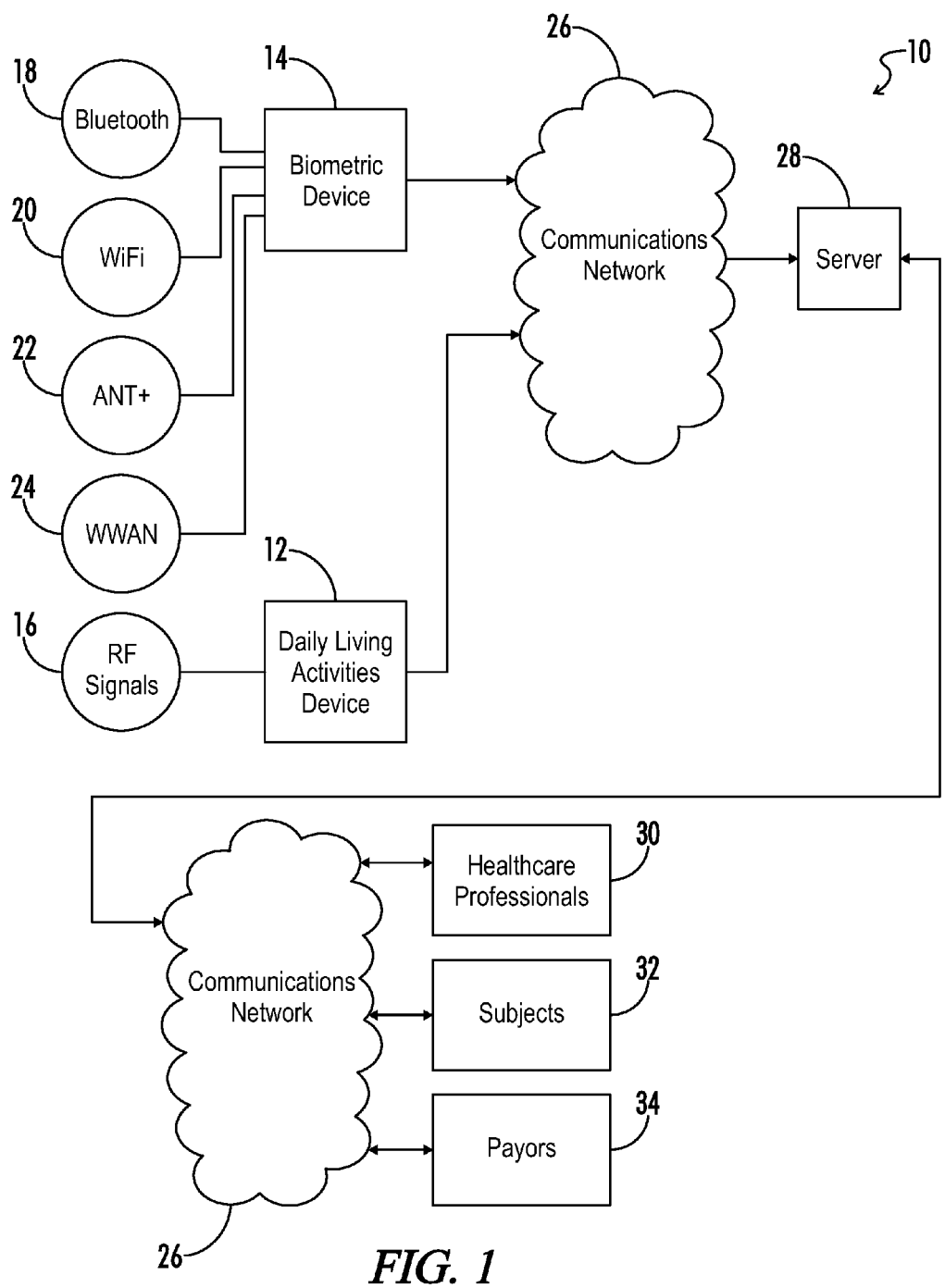
FIG. 1 is a block diagram representing an embodiment of a system in accordance with the present disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Referring generally to FIGS. 1-11, exemplary embodiments of devices, systems and methods for automatically assessing healthcare needs, facilitating healthcare resource allocation and generating a hosted user interface according to the present disclosure may now be described. Where the various figures may describe embodiments sharing various common elements and features with other embodiments, similar elements and features are given the same reference numerals and redundant description thereof may be omitted below.

Figure 2:
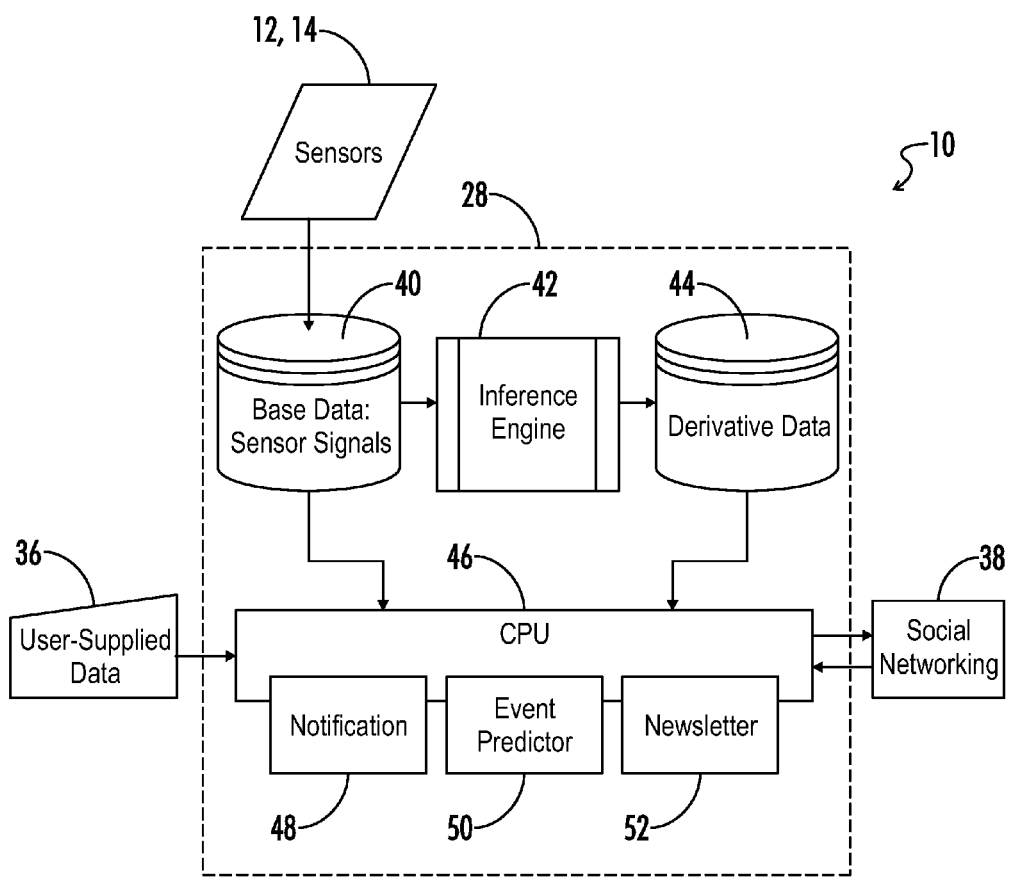
FIG. 2 is a block diagram representing another embodiment of a system in accordance with the present disclosure.

Referring more particularly first to FIGS. 1 and 2, an exemplary embodiment of a host system according to the present disclosure (e.g., a Smart Remote Monitoring System) may reside on a central server 28 and include one or more data processors 46 and computer-readable media functionally linked via a communications network 26 to a plurality of sensors 12, 14 as data sources. One primary market for the host system as disclosed herein may be senior citizens, but one of skill in the art may appreciate that the functions described herein may be more broadly applied to any individual requiring a professional or non-skilled caregiver, as well as to total population health applications.

The host system may be implemented in various settings, including but not limited to one or more facilities each having a plurality of integrally disposed inpatient residential areas, or a more distributed network of residential areas which are outside of a conventional healthcare facility but wherein subjects receive home healthcare treatment and may still be remotely monitored and assessed with respect to acute needs. In one embodiment, the system may include one host server that directly communicates with each sensor and remote or third party communications device, for example in the context of a single facility. In another embodiment, the system may include a plurality of distributed and communicatively linked servers, such as for example a first host server to perform data storage, diagnostics, prediction, etc., as further described herein, and one or more distributed servers to coordinate remote data collection and transmission with respect to various facilities, distributed residential areas, or the like.

The term "communications network" as used herein with respect to data communication between two or more parties or otherwise between communications network interfaces associated with two or more parties may refer to any one of, or a combination of any two or more of, telecommunications networks (whether wired, wireless, cellular or the like), a global network such as the Internet, local networks, network links, Internet Service Providers (ISP's), and intermediate communication interfaces.

The term "user interface" as used herein may unless otherwise stated include any input-output module with respect to the hosted server including but not limited to web portals, such as individual web pages or those collectively defining a hosted website, mobile desktop applications, telephony interfaces such as interactive voice response (IVR), and the like. Such interfaces may in a broader sense include pop-ups or links to third party websites for the purpose of further accessing and/or integrating associated materials, data or program functions via the hosted system and in accordance with methods of the present disclosure.

An exemplary host system, such as for example a Smart Remote Monitoring System ("Smart-RMS") as represented in FIG. 2, may without otherwise expressly limiting the scope of the present disclosure be a system for monitoring, gathering and analyzing data collected from or within a remote monitoring device network. The system generally uses an array of sensors and devices 12, 14 communicatively linked to a host server 28 to collect base data 40 associated with a subject (i.e., patient, senior, or other individual being monitored) within a given area. The data collection process by the sensors may be conducted in an entirely passive manner, meaning that it requires no conscious activity from the subject unless specifically noted herein. The base data 40 may be run through an inference engine 42 that generates derivative data 44. A series of algorithms may be executed by data processors 46 to utilize the base and derivative data and enable system capabilities, including but not limited to event notification 48, event prediction 50, and reporting 52.

More particularly with reference to FIG. 1, in one embodiment a host system 10 combines a device 12 for reporting activities of daily living with a biometric reporting device 14. These two separate devices and accompanying sensors may in various embodiments be joined to utilize a single network over which both types of data can be sent, thereby establishing a more comprehensive smart remote monitoring system 10. A daily living activity report device 12 for a system 10 as represented in FIG. 1 may receive a number of for example RF signals 16 representing the current status of subject activity. Exemplary activity sensors for implementation by a daily living activity reporting device 12 may include without limitation motion detectors, door contacts, flood (flush) detectors, pressure sensors (for bed and chair), Personal Emergency Response Systems (PERS) which require conscious activity, Active PERS which may (but not necessarily) be triggered by conscious activity, smoke detectors, carbon monoxide detectors, and the like.

The biometric device 14 may include or otherwise support inputs from designated medical devices using protocols such as Bluetooth 18, WiFi 20, ANT+ 22, or WWAN 24, any one or more of the inputs indicating a respective biometric status for the subject. Biometric input data may be provided from devices including without limitation blood pressure cuffs, weight scales, glucose meters, pulse/oximeters, and the like.

The base data 40 from the various sensors may further be associated with or otherwise be stored in the system corresponding to time and date stamps and/or equivalent information.

The devices 12, 14 may be coupled to a sensor communications hub (not shown) that is further linked to the server 28 via the communications network 26. The server 28 further may be communicatively linked via graphical user interfaces generated for or otherwise on behalf of for example healthcare professionals 30, subjects 32 and associated payors 34.

In an exemplary embodiment, the biometric reporting device may include or otherwise implement a Qualcomm 2Net® hub, and the activity reporting device may include or otherwise implement functionality from Resolution Products. The addition of the Resolution Products hub extends the capabilities of the 2net hub to include receiving and transmitting RF signals, which the 2net hub does not otherwise do. It may be understood that other devices may in certain embodiments be utilized to accomplish the same or equivalent features, and the examples shown and described herein may be considered as illustrative in nature, rather than limiting on the scope of the present disclosure.

The system generally, and more particularly the generation of derivative data for the purpose of implementing algorithms as disclosed herein, may optionally be enhanced through the use of user-input data 36 and social networking-generated data 38. These data sets are used in aggregate and in various combinations to enable features according to various embodiments of the present disclosure. In an embodiment, the host system may be integrated with one or more social media accounts. The integration of social media with the host system may be provided passively based on data and thresholds stored in association with the system. No direct action is necessarily taken by the subject in order to initiate the post. Rather, specific base and/or derivative data are flagged to be presented within social media accounts on behalf of the subject based on either an instance of the data (i.e. a PERS button push), or an established threshold(s) for the data (i.e. Amount of time out of bed exceeded, Number of pantry accesses exceeded, etc.).

The system optionally enables status updates to be made to the account by caregivers. These updates may in various embodiments be uploaded directly via a hosted web portal, e-mail, SMS text or directly through social media applications or other digital communications.

In typical implementations, the subject has no access to directly post to the social media accounts which are being posted on their behalf. Optionally, the subject may be accorded access to the account to post. Exemplary logic for an associated algorithm may include: If [NOTE ENTERED BY CAREGIVER], then [APPEND TO CARE NOTES], wherein caregiver notes may be System-Generated Alerts.

In various embodiments, an algorithm/program module of the system according to the present disclosure may take the aggregated daily living activity ("ADL") data and the derivative inferences and aggregate them into a periodic snapshot of the data. For example, active living signals may be aggregated over time to determine the amount of time a residence is occupied, or even further to separately identify an amount of time in residence and in bed. In addition to providing continuous feedback for various algorithms as further described below, such aggregated data snapshots or "newsletters" may serve as a baseline and record of the evolution of the senior's ADL over time. The amount of time spent "away" or outside of the residence may be significant, for example, as providing a metric of how socially engaged a subject is in a community and as an indicator of both health and contentment with a current living arrangement. Further, the aggregated snapshots may serve as indicators of caregiver performance as well, with respect to for example encouraging the subject patient to be more active in the community. In one embodiment, the newsletter may be customized by the presenter or may be customized by the recipient. In an embodiment, the newsletter may give higher priority in presentation of data (base or derived) that falls outside of established parameters for norms/standards. In an embodiment, the newsletter may provide status updates regarding the integration of the passively-generated social media.

Exemplary logic for prioritizing presentation of data may include without limitation:
If [DATA VALUE]< >[ESTABLISHED PARAMETERS], then [ASSIGN HIGHER PRIORITY]

In an embodiment, the host system of the present disclosure may serve as a time clock allowing caregivers to clock in and clock out with the addition of an input device (i.e. PC, smartphone, tablet, etc.). This function may optionally use a PIN or other unique ID code to protect against fraudulent entry. A "hyper-validation" feature may be used during a period of time during which a caregiver has been reported and/or is scheduled to be on site and/or a caregiver has logged in. An associated "EVV Hyper-validation" algorithm analyzes motion sensors, door contacts and other devices within the monitoring area for simultaneous signals that overlap (i.e. are received with the same or nearly the same time/date stamp) to determine if the monitoring area is occupied by more than the number of persons for whom care is being provided. Exemplary logic may include without limitation:
With Log In
If [EVV LOGIN] AND [NO EVV LOGOUT] AND THEN [PERIMETER ACTIVITY] AND [SIMULTANEOUS ACTIVITY], then [HYPER-VERIFICATION=TRUE]
If [EVV LOGIN] AND [NO EVV LOGOUT] AND [PERIMETER ACTIVITY] AND [NO SIMULTANEOUS ACTIVITY], then [HYPER-VERIFICATION=FALSE]
Without Log In
If [PERIMETER ACTIVITY] AND THEN [SIMULTANEOUS ACTIVITY], then [HYPER-VERIFICATION=TRUE]

In an embodiment, a system according to the present disclosure may require a caregiver who has logged in to respond to a series of questions for the purpose of determining that the person was on site and/or for the purpose of ADL assessment and/or medical assessment. The type of validation can be geared to the specific skills attributed to the caregiver. For example, a skilled nurse may be presented with healthcare questions that are of a more measured nature.

The SSRMS has established a set of derivative data that may be used for validating responses to systems requiring data input by the senior and/or by a caregiver. The use of core or derivative data to verify or underscore the accuracy of the data input is part of the claim for the SSRMS.

Systems may ask questions and compare the input responses to known values based on base and/or derivative data sets, including but not limited to those related to, e.g., sleep time, toilet usage, pantry/refrigerator access, time spent in an area or outside of an area, frequency of activity and/or an activity, compliance (i.e. wearing of a PERS device), etc.

Exemplary logic may include without limitation:
If [INPUT_RESPONSE]=[BASE_DATA VALUE], then [VALIDATE]
If [INPUT_RESPONSE]=[DERIVED_DATA VALUE], then [VALIDATE]

Figure 3:
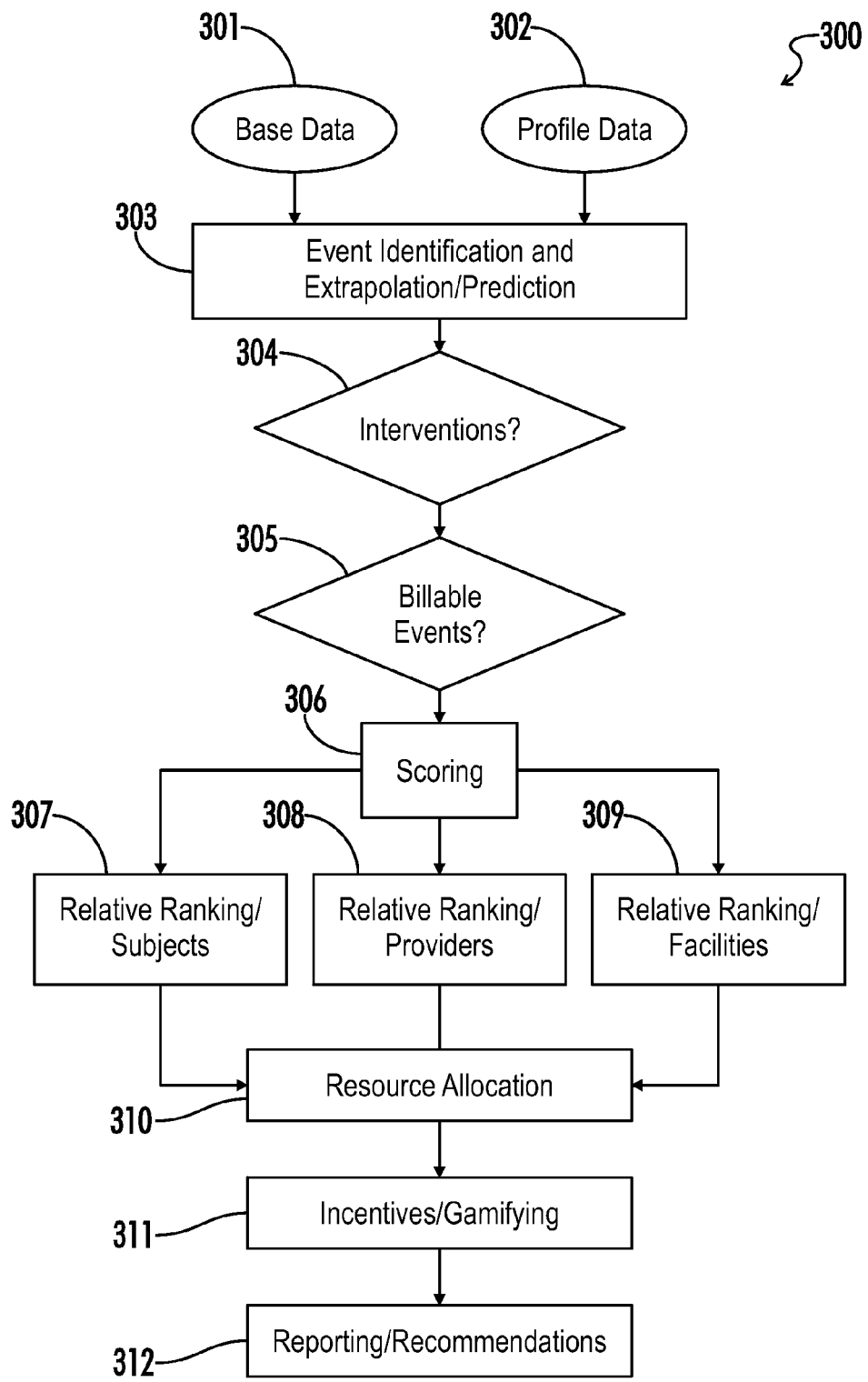
FIG. 3 is a block diagram representing exemplary program modules, engines and associated process flow for a system according to the present disclosure.

Referring now to FIG. 3, an exemplary method 300 is represented as may be implemented by a host system according to the present disclosure. The method 300 generally begins with or otherwise includes generally steps for receiving base data 301 from biometric and living activity sensors, and profile data 302 for a particular subject. The profile data 302 may be provided from any number of sources including but not limited to user input, social networking, third party HIT sources, medical records, and the like. Generally speaking, the profile data may further include a list of conditions for which the subject is considered to be at-risk or otherwise for which the subject should be directly monitored. This may be determined by the system based on the age, medical history, pharmaceutical history, demographics, etc., of the subject, or may be directly provided from one or more caregivers or even for example authorized family members.

In one exemplary embodiment, the host system further includes or has access to databases or equivalent data repositories wherein various conditions are further associated with predetermined event determination sequences. In other words, the system may effectively leverage stored data to determine the actual or likely presence of an event based on the input data in real-time from biometric and activity sensors, further in comparison with a predetermined sequence of one or more data points as determinative of an event and likewise a condition for which the subject is considered at-risk (step 303). As one example, a particular data point (subject opens front door at a given time) may be a primary data point in that is directly monitored and quantified, whereas this data point may take on more relevance in the context of the time itself (e.g., 2 o'clock in the morning) and the at-risk condition of a particular subject (e.g., one at risk of dementia).

An exemplary analytics process based on primary data points and with respect to time may include a measure of the amount of time spent in an area (e.g., room, bed, chair) on a daily basis, e.g., in intervals of seconds, minutes, hours, etc. Another exemplary analytics process may include a measure of the number of times an area (i.e. room, bed, chair) was "in use" during a given measure of time. Another exemplary analytics process may capture the number of defined time periods (i.e. every 5, 10 or 15 minutes) during which activity was detected in an area (i.e. room, bed, chair) relative to another given time period (i.e. daily, awake hours, bedtime hours). Yet another exemplary analytics process may measure the frequency an area (i.e. room, bed, chair) was "in use" relative to other areas. As further disclosed herein, the combination of primary data points and program algorithms may generally be provided for basic monitoring, high risk situations, post-even monitoring, identifying relevant trends, triggering intervention or emergency response alerts (step 304) and further generally supplement the subject profile for future diagnostics.

Intervention Determination

Various examples of even identification and extrapolation in the context of generating intervention alerts may be described next with reference to FIGS. 4-8. The term "intervention" in the context of the algorithms disclosed herein may unless otherwise stated define a prompt for intervention made to a caregiver or other person/agency with the authority to act in the best interest of the subject. This prompt may be issued by various methods including but not limited to an alarm, an SMS, e-mail, posting on a web site, phone call, paging system or other means of communication.

Figure 4:
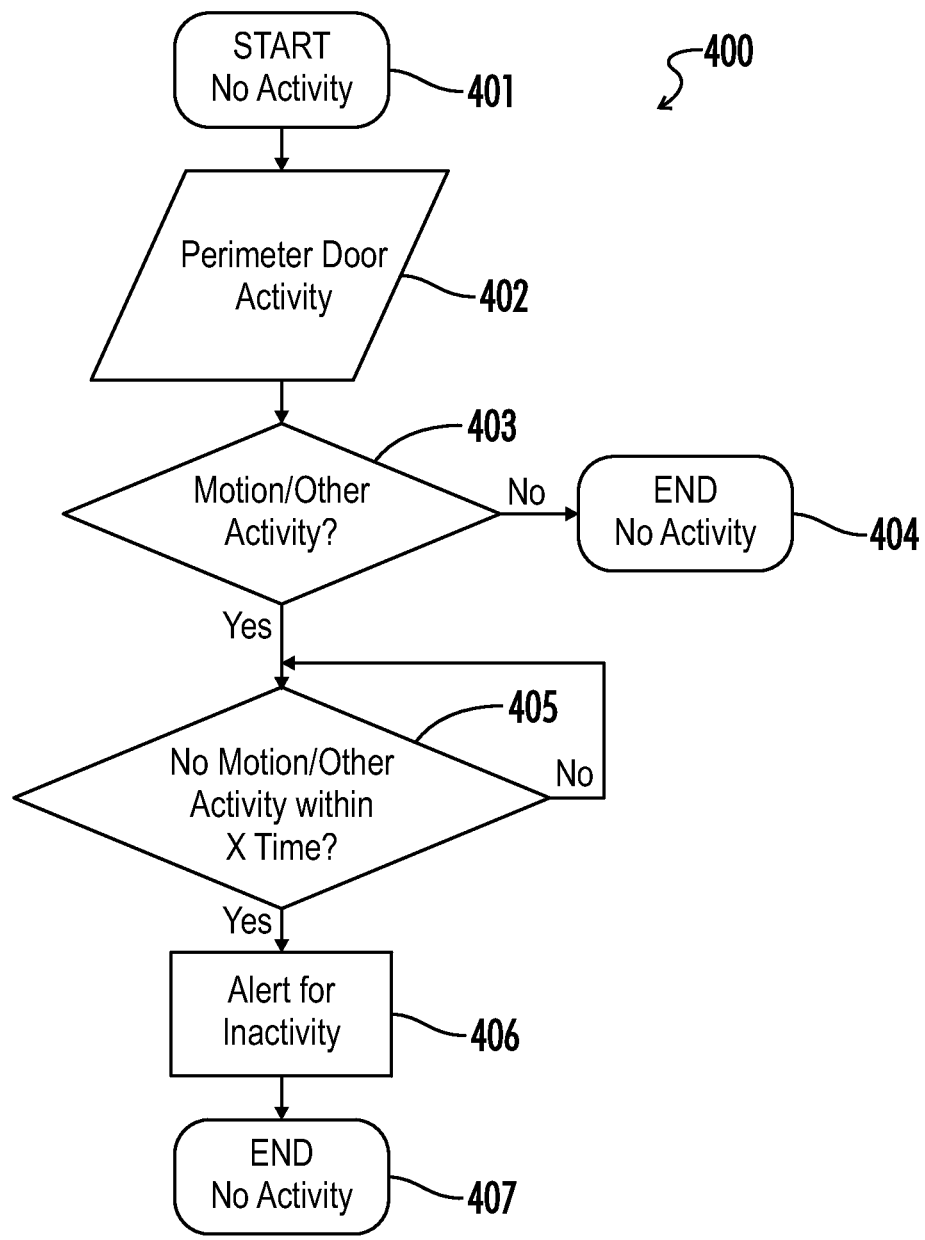
FIG. 4 is a flowchart representing an exemplary activity detection process performed by a system of the present disclosure.

Referring to FIG. 4, the system in one embodiment may perform diagnostics on input data to alert a caregiver to a potentially life threatening event warnings based on lack of activity during a defined period of known activity. An exemplary "No Activity" algorithm in accordance with this embodiment may monitor a combination of motion, door contact and/or pressure pad sensors in a target space for a lapse in activity during what is typically a time of activity. Parameters may be set and/or inferred (e.g., based on predetermined criteria and/or machine learning algorithms) to determine an acceptable period of activity to accommodate napping or other non-emergent situations. An example of the base logic may include the following:
  If [NO PERIMETER ACTIVITY SINCE HISTORIC ACTIVITY] AND [NO ACTIVITY] for [TIME], then [INTERVENTION]

Exemplary derivative data used and/or generated may include a "last historic activity," i.e., establishing a time at which the last activity was detected other than perimeter door activity. A further exemplary "Perimeter Activity" algorithm (not shown) may utilize a door/window contact(s) to monitor a senior's home for a breach of the exterior. The primary algorithm functions during bedtime hours which can be a derivative and/or user input value.

Figure 5:
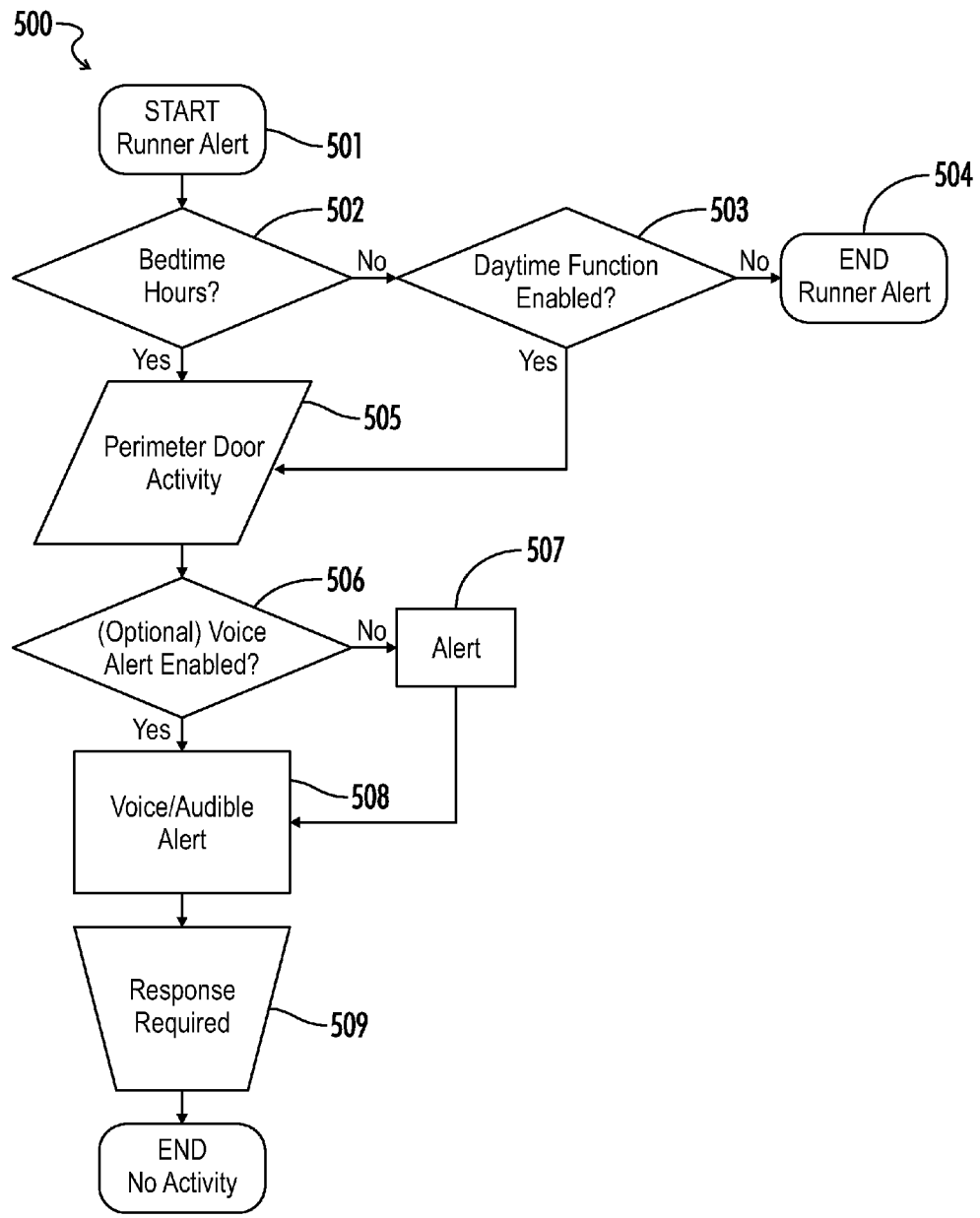
FIG. 5 is a flowchart representing an exemplary runner alert process performed by a system of the present disclosure.

Referring to FIG. 5, the system in one embodiment may perform diagnostics on input data to alert a caregiver if a perimeter breach occurs during a time deemed unacceptable. An enhanced algorithm with "Runner Alert" algorithms may further encompass non-bedtime hours as well (e.g., step 503), and may include an audible voice warning. This function may be used to monitor for "Runners" or "Wandering" as associated with dementia or other health issues. An example of the base logic may include the following:
  If [BED TIME HOURS] AND [PERIMETER ACTIVITY], then [INTERVENTION].

This function can be enhanced to include a verbal warning for a caregiver with responsibility for the patient (e.g., steps 506, 508). When enabled, the Dementia Enhancement would emit a verbal warning that a perimeter breach had occurred. Exemplary logic with dementia enhancement may include:
  If [PERIMETER ACTIVITY], then [AUDIBLE WARNING] AND/OR [INTERVENTION].

Exemplary derivative data used and/or generated may include a "sleeping time," e.g., a measure of the amount of time slept based on a bed being occupied, and may be aggregated into time periods by day, week, month, and/or day of week. This function can be optionally enhanced with the inclusion of motion detection sensor data indicating activity in the room.

A "Pantry Activity" algorithm (not shown) may be provided which utilizes a sensor (door contact and/or motion detector) to quantify the volume and frequency of access to, e.g., one or more pantry/cupboard(s) and/or a refrigerator.

Derivative historical values and/or input values may in various embodiments establish thresholds utilized by a system and method as disclosed herein to identify trends and/or variations in eating habits. Significant variations or breaches of thresholds may result in prompt(s) for intervention being issued. Alternatively, thresholds may be established and prompts for intervention issued when thresholds are breached. This function may be utilized to, e.g., identify and monitor dietary habits, identify/diagnose overeating, malnourishment or other eating disorders, identify/diagnose other health-related issues that have sleep disorder as a symptom, monitor other health-related issues that have sleep disorder as a symptom, or the like.

Exemplary derivative data used and/or generated may include "Pantry Raid or Neglect" data, wherein the system measures the number of times a pantry or other food storage area was accessed within a given time period (i.e. daily, weekly, during awake hours, during bedtime hours). The data may be constrained to absolute indicators of access or aggregated by instances of access within a time period (i.e. 5, 10, 15 minute intervals). The "Pantry raid or Neglect" data may be calculated with respect to various time periods including but not limited to: time of day, meal times, day, week, day of week, etc.

A "Nighttime Pantry Access" algorithm (not shown) may be provided which cross-references derivative and/or input values for the bedtime hours with "Pantry Access" data to identify nighttime eating habits.

Figure 6:
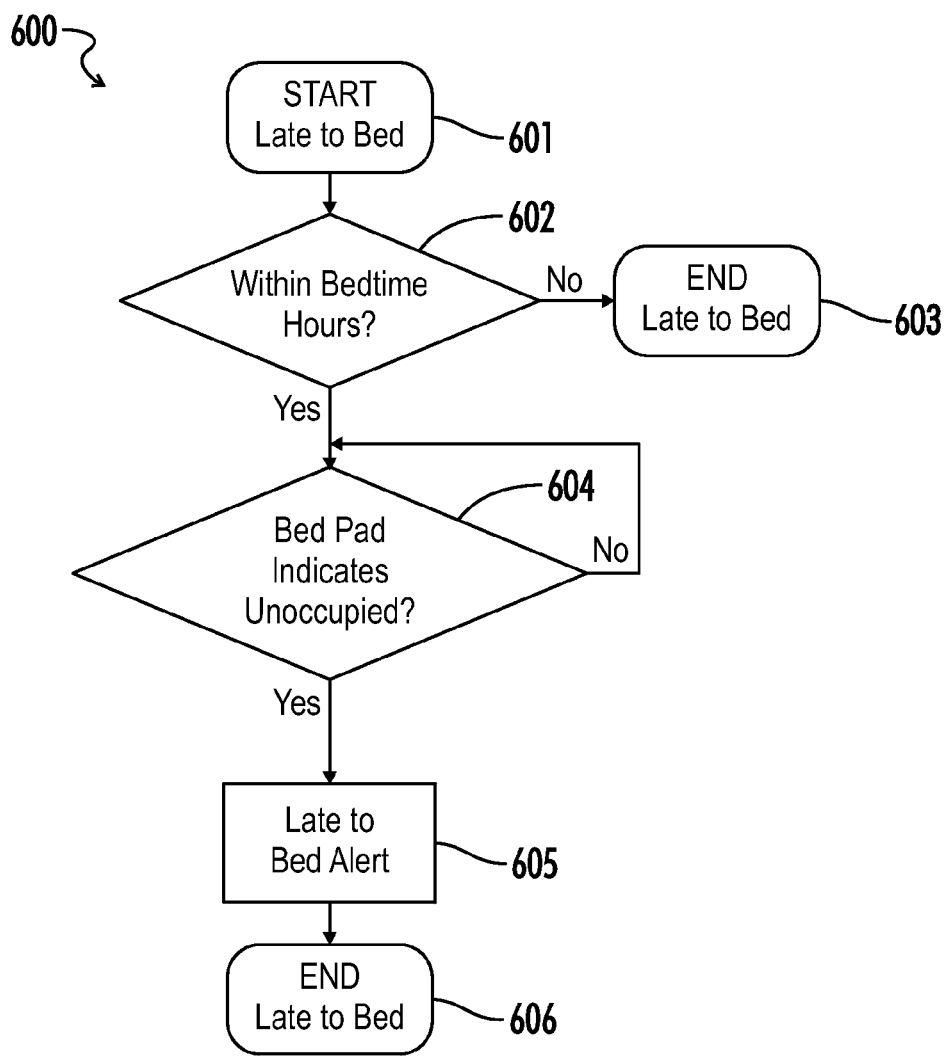
FIG. 6 is a flowchart representing an exemplary "late to bed" monitoring process performed by a system of the present disclosure.

Referring to FIG. 6, the system in one embodiment may perform diagnostics on input data to alert a caregiver if a subject is late to bed. A "Late to Bed" algorithm may be provided which in conjunction with appropriate sensors and communication network components may be executed to monitor the bed pressure pad, to determine instances where a senior may be late getting to bed, and to determine the acceptable late time period(s). The "late to bed" algorithm establishes a variable(s) that is learned and modified over time as sleep habits change and/or evolve. It can be initialized, overridden and/or enhanced with user input data. This function may be utilized to, e.g., identify and monitor general sleep habits, sleep disorders, other health-related issues that have sleep disorder as a symptom, etc. An example of the base logic may include the following:
  If [BED NOT OCCUPIED] AND [LATEST TIME TO BED], then [INTERVENTION]
  If [BED NOT OCCUPIED] AND [LATEST TIME TO BED] AND [NO ACTIVITY], then [INTERVENTION]

This function may in various embodiments be further used for the purpose of determining an appropriate time to enable a "Fall Detection by Logic" algorithm, as described in greater detail below and with reference to FIG. 8.

Exemplary derivative data used and/or generated may include "Time to Bed" data, which captures the time at which a bed is initially occupied each evening and may be aggregated for analysis by day, week, month and/or day of week. Further exemplary derivative data may include "Latest Time to Bed" data, as a calculated value that determines expected variations in a person's going to bed time based on historical values for day, week, month and/or day of week.

Figure 7:
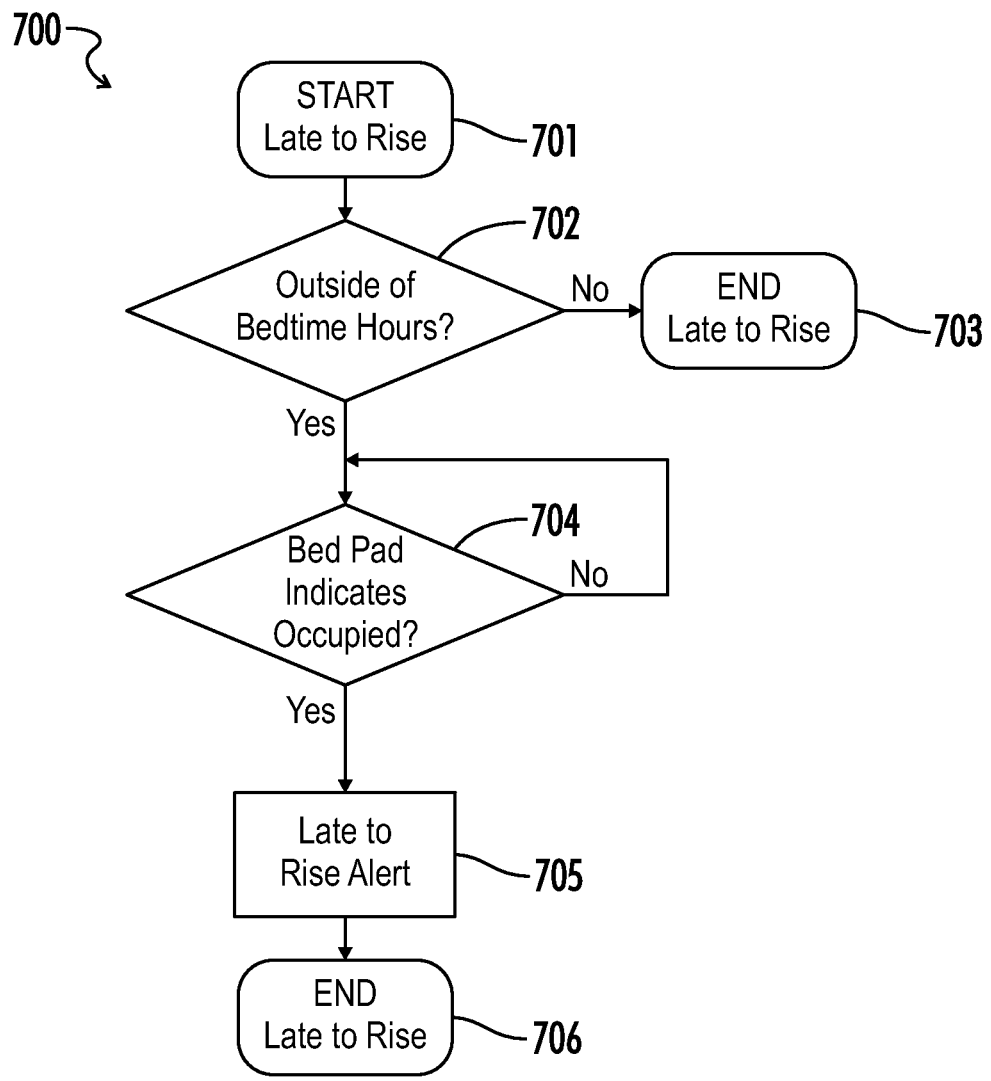
FIG. 7 is a flowchart representing an exemplary "late to rise" monitoring process performed by a system of the present disclosure.

Referring to FIG. 7, the system in one embodiment may perform diagnostics on input data to alert a caregiver if a subject is late to rise. A "Late to Rise" or "Snooze" algorithm may be provided which monitors the bed pressure pad to determine instances where a senior may be late to arise from the bed and determines the acceptable late time period(s). The Snooze algorithm establishes a variable(s) that is learned and modified over time as sleep habits change and/or evolve. The function can be calibrated by day of week, time of year, etc. An example of the base logic may include the following:

If [BED OCCUPIED] AND [AFTER TIME TO RISE+ SNOOZE], then [INTERVENTION]

If [BED NOT OCCUPIED] AND [AFTER TIME TO BED] AND [NO ACTIVITY], then [INTERVENTION]

Exemplary derivative data used and/or generated may include "time to rise" data which captures the time at which a bed is initially vacated each morning and may be aggregated for analysis by day, week, month and/or day of week. Further exemplary derivative data may include "snooze" data as a calculated value that determines expected variations in a person's waking time based on historical values for day, week, month and/or day of week.

A "Variation in Sleep Time" algorithm (not shown) may be provided which determines if a senior's amount of sleep is varying. Historical values are compared against current individual and/or aggregate values to determine deviations. An example of the base logic may include the following:

If [CURRENT WEEK SLEEP TIME]< >[CURRENT WEEK-1 SLEEP TIME], then [SLEEPING LONGER ALERT]

If [CURRENT WEEK SLEEP TIME]< >[CURRENT WEEK-2 SLEEP TIME], then [SLEEPING LONGER ALERT]

If [CURRENT WEEK SLEEP TIME]< >[CURRENT WEEK-3 SLEEP TIME], then [SLEEPING LONGER ALERT]

If [CURRENT WEEK SLEEP TIME]< >[CURRENT WEEK-4 SLEEP TIME], then [SLEEPING LONGER ALERT]

Figure 8:
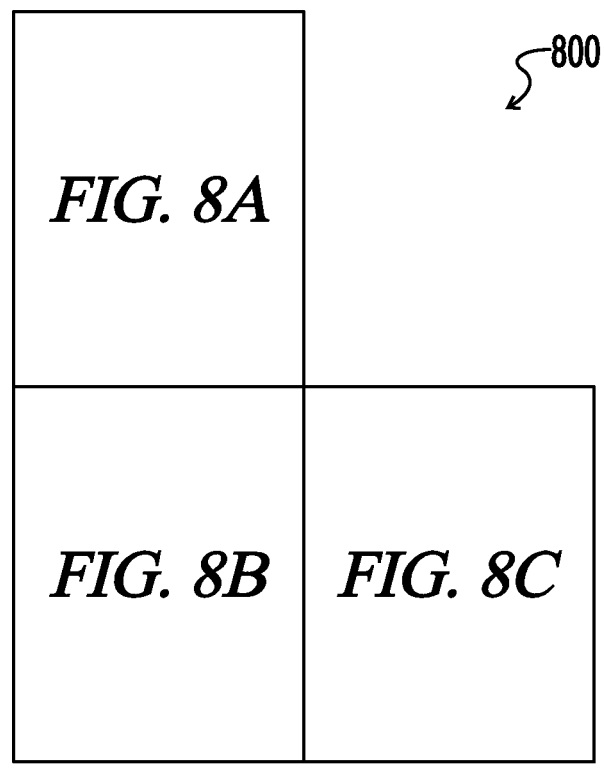
FIGS. 8A to 8C collectively are a flowchart representing an exemplary "fall detection by logic" process performed by a system of the present disclosure.
Figure 8A:
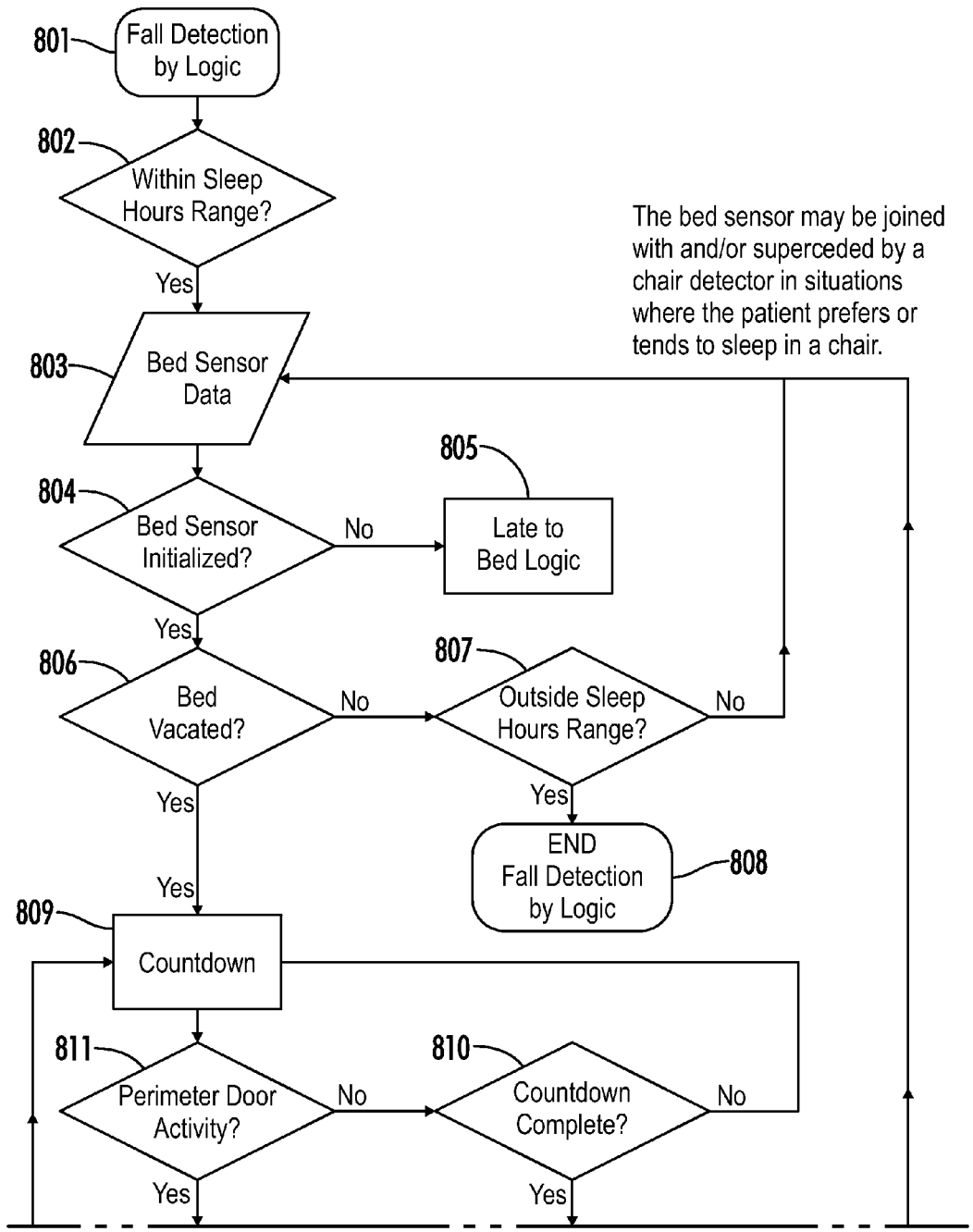
Figure 8B:
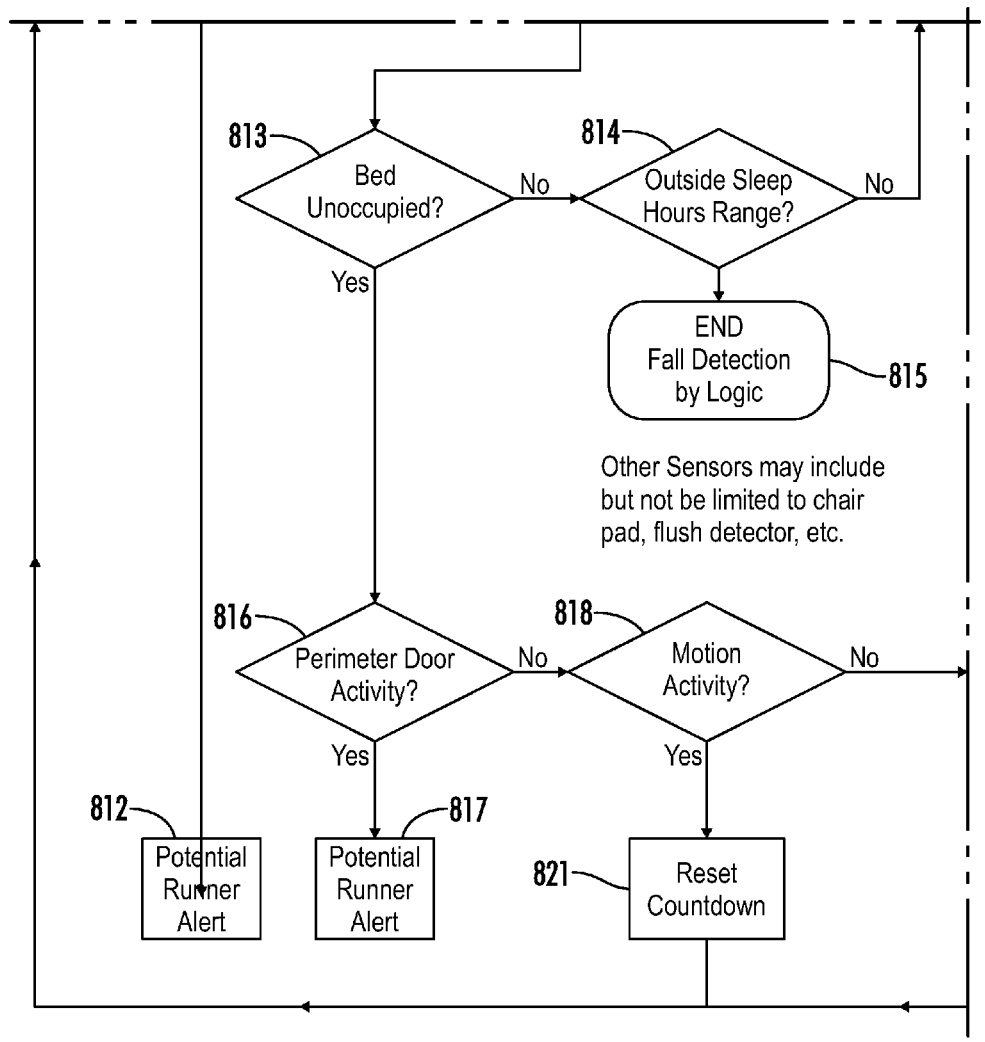
Figure 8C:
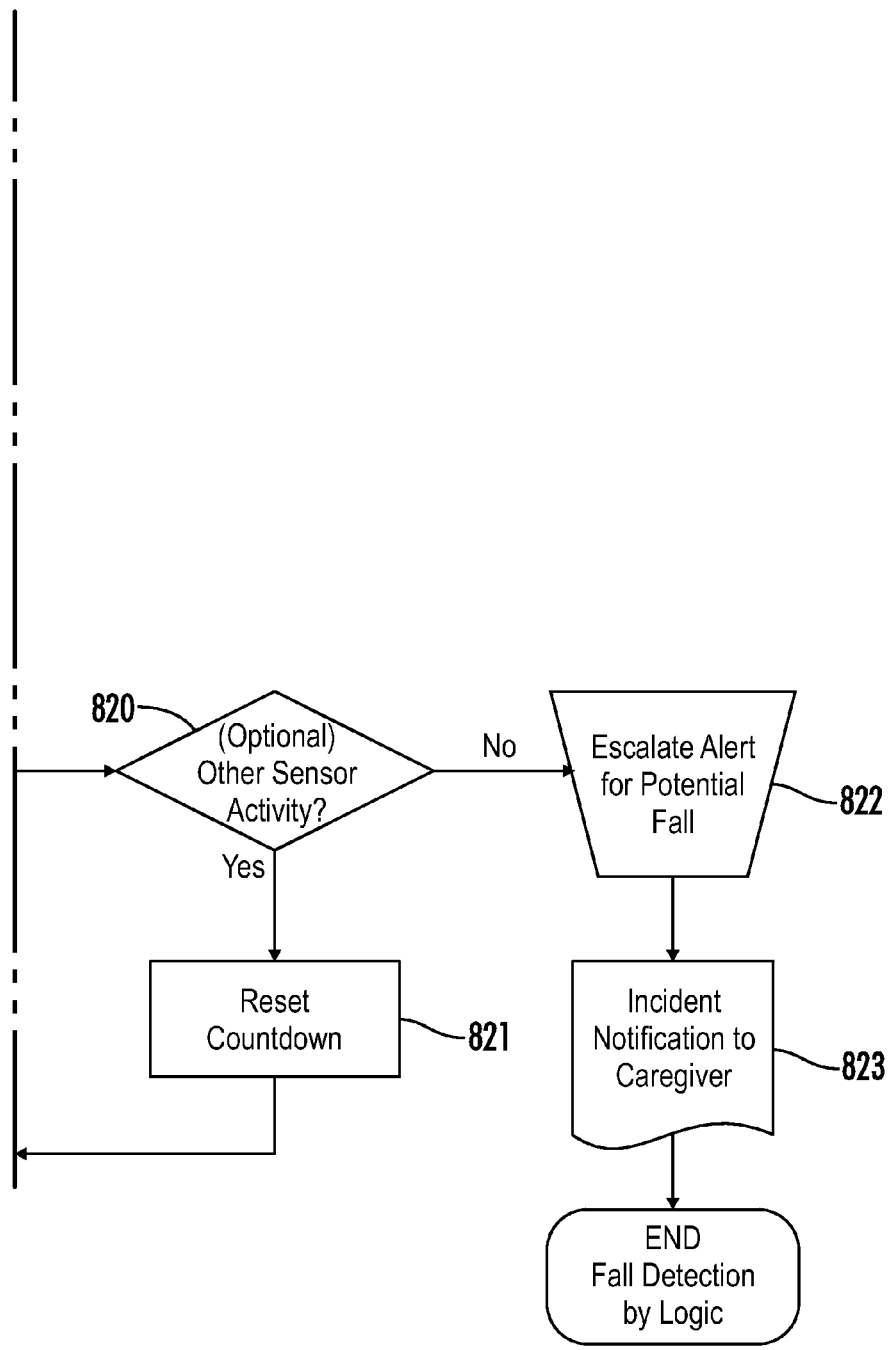

Referring to FIG. 8, the system in one embodiment may perform diagnostics on input data to offer nighttime fall detection without the need for a Personal Emergency Response System (PERS) or other notification device. A "Fall Detection by Logic" algorithm determines if a potential nighttime fall has occurred. The algorithm monitors the bed pressure pad during sleeping hours for periods of vacancy accompanied by a lack of activity from other sensors to indicate that a subject may have fallen. The addition of an Active PERS device may allow this algorithm's functional time period to be extended to cover periods of time when the Active PERS device is not being worn. This function may be utilized to, e.g., monitor for and identify falls, comprehensively capturing nighttime falls including those that previously may have gone unreported. Falls may further be determined in combination with a "no activity" algorithm as previously described.

Additionally, an Active PERS device in various embodiments comprehensively captures instances of falls outside of the fall detection by logic algorithm including those that previously may have gone unreported. The indication of a fall by any one or more of the Fall Detection by Logic, No Activity and Active PERS may be used to cross-validate in instances where a fall is detected by more than one method. For added accuracy, detected falls may be confirmed individually or collectively through communication with the senior, insurance claims, medical records, caregiver communication or other means. Collectively or individually, these captured falls may be used to predict future falls.

In its most raw form, detected falls are aggregated and used as a means to indicate a predisposition for future falls. This is a methodology consistent with the fall scoring as currently known in the art, but is more accurate than the current method which currently depends on self-reported incidences which represent less than 50% of the actual incidences. A system according to the present disclosure may anticipate future falls based on the comprehensive data set and allow additional and more severe subsequent falls to be monitored, minimized and/or averted through intervention and/or previous knowledge of a patient in an at risk situation.

In various embodiments, a "Fallcasting" algorithm (not shown) may quantify by amount of time of inactivity following a fall event utilizing other sensors in the home such as motion detectors, door contacts, chair pads and bed pads. These periods of inactivity are used to calculate the severity of a captured fall(s) and are factored into the likelihood of a future fall(s) and the severity of that/those future fall(s). This algorithm may typically compare an individual's data to established benchmarks among control groups.

Another more advanced algorithm may be provided or otherwise implemented which utilizes the activity score provided by the Active PERS device to compare the relative activity level of the senior pre- and post-fall event. This scoring may be used by clinicians and/or health plans to prioritize the need for intervention where a significantly lower score post-event is indicative of a higher need for intervention such as physical therapy (e.g.). This algorithm compares a patient's relative individual scores and/or compares the relative scores to established benchmarks among control groups.

Activity scores post-event may be evaluated among groups (demographic, regionally, by health plan, etc.) as well as relatively among other defined groupings. The system may further calculate the number of falls preceding a hospitalization due to a fall. This data is applied against demographic data (including but not limited to age, gender, geographic location, diseases, co-morbidities, race, etc.) to determine if a greater likelihood of a fall exists for an individual based on their demographic profile.

While this alert is generally deployed during bedtime hours, it can be manually extended to provide more comprehensive coverage. An example of the base logic may include the following:

If [NO PERIMETER ACTIVITY] AND [BEDTIME HOURS] AND [BED VACATED] AND [TIME ELAPSED] AND [ACTIVITY], THEN [RESET TIMER]

If [NO PERIMETER ACTIVITY] AND [BEDTIME HOURS] AND [BED VACATED] AND [TIME ELAPSED] AND [NO ACTIVITY], THEN [INTERVENTION]

This could be done with the second portion as an ELSE option.

Exemplary derivative data used and/or generated may include "time to bed" data which captures the time at which a bed is initially occupied each evening and may be aggregated for analysis by day, week, month and/or day of week. Further exemplary derivative data may include "latest time to bed" data as a calculated value that determines expected variations in a person's going to bed time based on historical values for day, week, month and/or day of week. Further exemplary derivative data may include "time to rise" data which captures the time at which a bed is initially vacated each morning and may be aggregated for analysis by day, week, month and/or day of week. Further exemplary derivative data may include "snooze" data as a calculated value that determines expected variations in a person's waking time based on historical values for day, week, month and/or day of week. Further exemplary derivative data may include "nightly toilet usage" data as a detected daily, weekly, monthly aggregate number of instances of toilet usage during bedtime hours. Further exemplary derivative data may include "inferred nightly toilet use" as a determined daily, weekly, monthly aggregate number of instances of toilet usage during bedtime hours based on number of times a bed is vacated. The data may be enhanced through elimination of instances of vacated bed when sensors detect other activity (i.e. kitchen motion). The data may further be enhanced to constrain number of instances within a given time period (i.e. 5, 10, 15 minutes).

A "toilet use" algorithm (not shown) may be provided in accordance with the present disclosure which utilizes the bed pressure pad and/or the flood/flush detector to monitor bathroom usage. For nighttime, a bed pad indicating that the bed has been vacated during sleep time hours is the core indicator. The addition of the flush monitor enhances the ability of the algorithm to predict that bathroom usage is the reason for vacating the bed. This function may be utilized to, e.g., monitor and identify for incontinence or related-health issues such as potential falls, bladder infection, etc. This feature may further enhance the logic of the Fall Detection by Logic algorithm. An example of the associated logic may include the following:

If [BEDTIME HOURS] AND [BED VACATED], then [INFERRED TOILET USE+1]
If [BEDTIME HOURS] AND [BED VACATED] AND [TOILET FLUSH], then [TOILET USE+1]
If [BEDTIME HOURS] AND [BED VACATED] AND [BATHROOM MOTION], then [TOILET USE+1]
If [BEDTIME HOURS] AND [BED VACATED] AND [TOILET FLUSH] AND/OR [BATHROOM MOTION], then [TOILET USE+1]

As referred to above, an Active PERS device typically utilizes an accelerometer to "score" movements. Movements that exceed a certain threshold are considered to be indicative of a fall. An Active PERS device may have a "reporting threshold" that can be modified to account for the level of activity by the wearer. The threshold may be necessary to avoid false positives and account for the wearer's level of activity. Scores below the reporting threshold are not reported (i.e. sent for intervention). In one particular embodiment of a system as disclosed herein, such a device may be a PAMSys™ sensor as offered by Biosensics and further as embodied in U.S. Pat. No. 8,206,325 for an "Ambulatory System for Measuring and Monitoring Physical Activity and Risk of Falling and for Automatic Fall Detection," herein incorporated by reference in its entirety.

In an embodiment of the present disclosure, a "Remind to Wear" algorithm monitors for compliance to ensure that the subject wears the device. Logic may be added to the device to detect periods of prolonged inactivity. Long periods of inactivity generate a prompt for intervention by the Active PERS device. The "Remind to Wear" algorithm prompts an alert to remind the wearer to wear their Active PERS device. The prompt may be actualized via e-mail, text, or other digital delivery method and/or phone call (automated or personalized). The "Remind to Wear" algorithm further filters the prompts to account for sleeping hours to avoid false positives. An example of the base logic may include the following:

If [NOT BEDTIME HOURS] AND [NO MOTION ACTIVE_PERS], then [INTERVENTION]

In an embodiment, an "Activity Scoring Active PERS" algorithm requires the "reporting threshold" be set lower to capture more of a wearer's daily activity. The algorithm filters the data for scores that are above the "fall detection threshold" to maintain the fall detection capability. The scores between the "reporting" and fall detection thresholds are used to generate a score indicating the level of activity of the wearer. The scores may be aggregated on different time periods which can be determined by a default value, a user input value or a learned value. The scores are presented as straight scores and/or are compared relative to one another to determine a change in the amount of the wearer's activity.

An "Activity Scoring" algorithm monitors the amount of activity exhibited by a senior within their ADL environment. Scoring can be done on an absolute, relative or mixed scoring basis. Activity is defined as motion logged via the motion detectors. Multiple signals of motion from alternating motion detectors would increase the rating. For subjects confined or primarily confined to an area, the activity score would be an absolute value. For seniors who leave the premises, scoring would be on a relative basis comparing one day to the next and accounting for time away as a period of assumed activity. While the activity outside of the home is not measured, the time spent outside of the home is assumed to include some activity on the senior's part. Exterior door openings where the senior can be logically deduced to have left the premises may be factored in.

The baseline value is established by user input values and/or learned values. A historical record of the activity is logged for subsequent analysis. Subsequent analysis may include without limitation identifying fluctuations in activity, variations in timing of activity, or the like. Optionally, a subject and/or a caregiver may rate their activity for a given day. This rating may optionally be used to calibrate the system, assess the subject's awareness and/or self-awareness, or the like. Optionally, an Active PERS activity score is analyzed in conjunction with the Activity Score from motion detectors. Optionally, seasonal conditions including temperature and weather conditions are used to calibrate the system.

Various challenges and/or limitations may include interference or false readings created via non-seniors on premises such as family or caregivers. Time spent outdoors by the subject will by its very nature not be factored into the analytics. Weather could be a factor (i.e. inside more in winter and outside more in summer). Analytics blended with ACTIVE PERS Motion could also be implemented as desired.

In an embodiment, the SSRMS may be configured to include functions based on a known senior disease state(s). These functions may be based on base data and/or derived data and/or the proprietary algorithms that evaluate that data. Some of these configurations may be as follows:

DEMENTIA
If [DEMENTIA]=YES, AND [ACTIVITY=CONSTANT], then [WANDERING ALERT]
If [PANTRY_ACCESS]<X, then [NOT EATING ALERT]
DIABETES
If [DIABETES=YES] AND [CUPBOARD ACCESS]>X, then [INTERVENTION ALERT]

DEPRESSION

If [DEPRESSION]=TRUE, AND [NO PERIMETER ACTIVITY WITHIN 24 HOURS], then [INTERVENTION ALERT]

If [NO ACTIVITY WITHIN 24 HOURS], then [INTERVENTION ALERT]

In an embodiment, a system according to the present disclosure may implement a Vigilant Mode which minimizes or eliminates any tolerances in the system for Fall Detection or other monitoring. Exemplary logic may include without limitation:

If [OUT OF BED THIS WEEK>OUT OF BED LAST WEEK], then [VIGILANT MODE]

Using historical data, it is possible to identify and categorize significant events and their associated time of occurrence. An analysis or review may be conducted for data that fall outside of a baseline and to flag those as indicators for the event. In an embodiment, a system according to the present disclosure may include and implement a disease prediction module, wherein analytics may be conducted to predict diseases such as dementia (future), exemplary logic for which includes without limitation:

If [DEMENTIA=YES] AND [ACTIVITY=CONSTANT], then [WANDERING ALERT]

Pattern recognition may be an integral factor in various aspects, but in many cases this feature may be difficult to accurately model. In certain embodiments, the system may apply pattern recognition in some known settings and establish patterns.

If [NO CUPBOARD ACCESS] OR [NO FRIDGE ACCESS], then [NOT EATING ALERT]

Other examples of diseases according to such an embodiment may be diabetes, depression, frailty, etc., each having associated derivative data, base logic, etc.

In an embodiment, a system according to the present disclosure may include post-even learning and event prediction program modules, wherein following an event (fall, stroke, heart attack, etc.) data may be reverse analyzed to identify changes in the data that preceded the event. Each event may be categorized to capture event specific data including, but not limited to, a type of event (e.g., fall, stroke, heart attack, number of instances thereof, etc.), date/time of occurrence, severity, outcome (as known), and the like. Demographic data about the subject may be included as available, including, but not limited to age, gender, race, location, and health-related data demographic data such as ADL scores, health risk assessment data, and recorded biometric scores such as blood pressure, weight, glucose and pulse/oxygen.

In various embodiments, analysis may be conducted on base and derivative data sets beginning at the time of the event and working backward in the logged data sets until a consistent value for the data set is reached. That consistent value and its time from the point of the event are defined as the data set benchmarks. Benchmarks can be absolute values and/or ranges. A benchmark can also be established for a data set based on system defaults, user input values and/or learned values. Data may be analyzed and sorted by time from the benchmark point in terms of absolute (raw measure) and relative variation (i.e. percentage change) from the benchmark.

Typically, data sets may be of three types—indicator, early indicator and non-indicator. In general, indicator data a data set with variations that ultimately converge to a consistent value or range. In general, early indicator data is an indicator data set that manifests a deviation from the benchmark earliest (furthest from the event) are considered "early indicators" and are used to identify potential events. As such, Early Indicator Data Sets are a subset of the Indicator Data Sets. In general, non-indicator data is a data set with no consistent values and/or values that have no appreciable change.

With respect to an event prediction module as referred to above, in various embodiments deviations within a data set from the data set benchmark are used as generic event predictors. The benchmarks are based on system defaults, user input values and/or learned values over time. If a subject breaches any of these benchmarked thresholds, a prompt for intervention is issued.

Alternatively, when a subject has a previous event and/or a common demographic group has a previous event benchmarks are used to establish appropriate ranges for the subject. If these ranges are breached, a prompt for intervention in anticipation of a specific type of event is issued.

Prompts may be graded according to the number of early indicators and indicators occurring. Subsequent higher priority alerts are issued if thresholds continue to be breached and/or additional data set thresholds are breached. The established data sets may be used as baselines for a subject to predict the potential for an occurrence/recurrence of an event. First time occurrences are based on a group analysis. Recurrences are based on subject-specific analysis as well as common demographic group analysis.

Generally stated, a subject has data set benchmarks that are unique to them. Subject-specific analysis is run against these benchmarks, and breaches of early indicator and indicator thresholds result in the issuing of a prompt for intervention.

In various embodiments, subjects may be compared against other subjects based on single or multiple common demographic data elements. Data sets are aggregated to determine which data sets are the most accurate indicators for a type of event for a given demographic group.

A data set that has early indicator data may generally issue a prompt for intervention. The prompt for intervention is given higher priority based on the existence of other early indicators or indicators. The prompt for intervention is given a lower priority based on the absence of other early indicators or indicators.

In various embodiments, for both generic and event-specific prediction, the sensitivity of a prompt for intervention may be adjusted in a number of ways. As one example, the system may change the number of indicator data sets required to trigger the alert. Sensitivity may be adjusted based on the margin of deviation from the benchmark (either absolute or relative values), or by the length of time elapsed that data set benchmarks have been consistently breached, by demographic comparison that suggests a higher or lower rate of incidence for a subject's given demographic(s), or by a subject's previously recorded event history, etc.

Billable Event Determination

Returning now to the method 300 represented in FIG. 3, the system may determine whether one or more directly identified or indirectly extrapolated events may be billable in nature (step 305). An assisted billing program module may implement system alerts as well as other data points and algorithms to create "billable events", exemplary alerts including, e.g., PERS button pushes and Fall Detection by Logic, Auto-Assessment scores (see below), meal delivery (with or without confirmation), dressing assistance, and the like.

In one example, a billing event may be automatically identified for assistance provided, such as where a subject resident presses an associated PERS button for assistance or Fall Detection by Logic is detected. The system may issue a prompt to bill for the event. Detected elopement (leaving residence during monitored hours) can likewise be a billable event. If the event has been logged and verified as an event, the prompt may in various embodiments be upgraded to an auto-billing, wherein information from the event can be forwarded.

In another example, a billing event may be identified based on changes in the level of care. One such case may be where an auto-assessment score for the subject increases or decreases. A prompt may be issued for a review of the care level provided in accordance with the billing practices of the facility. Another such case may be where the subject's auto-assessment ranking relative to other residents increases or decreases, wherein a prompt may be issued for a review of the care level provided in accordance with the billing practices of the facility. The system may in various embodiments recommend a specific change in care level based on a percentage change or absolute change in the auto-assessment score, and/or tie the auto-assessment score/ranking to a given care level and prompt for billing accordingly. This utilizes the manual assessment of care level in conjunction with the auto-assessment score feature.

In another example, a billing event may be identified in association with meal delivery. If a subject is detected as in bed and/or at home during mealtime hours, a prompt may be issued to bill for the event. If the event has been logged and verified as an event, the prompt can be upgraded to an auto-billing, wherein information from the event can be sent.

In another example, a billing event may be identified in association with an AM dressing assistance alert. If, e.g., (1) a subject status is "IN BED" during AM hours, (2) a door opens to the residence and motion is detected in the residence, (3) the bed is vacated more than x minutes later without door opening detected, and (4) the door opens again and status is AWAY, a prompt may be generated by the system for "help getting out of bed" and/or "help dressing", wherein a prompt is further issued to bill for the event. If verified as an event, the prompt can be upgraded to an auto-billing.

In yet another example, a billing event may be identified in association with a PM dressing assistance alert. Where, e.g., (1) a previous AM Dressing Assistance alert has been made and/or confirmed, (2) a door opens to the residence and motion is detected in the residence, (3) the bed is determined to be occupied, (4) motion is detected after the bed is occupied without the door opening, and (5) the door opens again and the status is "IN BED", a prompt may be issued to bill for the event. If verified as an event, the prompt can be upgraded to an auto-billing.

The system may upon categorizing an event as a potential billing event further cross-check the potential billable event against a list of actual billed events as may have been for example manually entered into the system. If a potential billable event has already been billed, the system does not proceed further. Likewise, if the system identifies a tag, note or equivalent manual entry associated with the type of billable event that instructs the system accordingly, the system does not proceed further. However, assuming the billable event is not redundant with respect to a previous entry, and is authorized as a potential billable event, the system may in one embodiment generate an appropriate notification and associated user interface that enables confirmation of the billable event. The system may as described above further enable user selection of an auto-billing feature for the same type of billable events in the future.

Auto-Assessment Ranking ("AAR")

The method 300 further includes generating scores and relative rankings for healthcare subjects (steps 306-309), as well as in certain embodiments the associated providers and/or facilities, for implementation of various features as disclosed herein. Scoring and relative ranking for each of a number of subjects in a defined group, such as for example would apply for each subject in a given facility or otherwise for which a defined group of healthcare providers are responsible, may be used in accordance with various embodiments of the present disclosure for generating resource allocation reports and/or recommendations, as well as providing a basis for event detection, incentives, etc.

In one embodiment, the Auto-Assessment Ranking (AAR) gives a relative ranking to each resident in a facility based on a series of measures captured by the system. Residents are "ranked" on a scale that indicates the relative level of assistance the resident requires. The relative ranking is used for a number of reasons. First, it allows the facility to identify the residents with more acute needs. Second, it allows the health of each individual resident to have their health evaluated in a "crowd-sourced" method. The best ranking attainable may be a score of 1, wherein the worst possible score can be adjusted according to the facility.

The ranking improves a facility's quality of care in many ways. For example, the Auto-Assessment Ranking can be used to identify high-need residents. Higher scores may typically be indicative of residents with more acute care needs, which may or may not include sleep issues, incontinence, fall history, reduced mobility, excessive calls for assistance, i.e., generally more acute care needs and/or generally higher consumption of staffing resources. The score may be used to identify residents for in-depth assessment of needs by staff, to establish a measure of care level related to billing purposes, or to identify residents whose care needs may need to be reevaluated.

A sudden change in a score and/or a relative ranking can be used to identify a resident whose particular situation may have changed. For example, a resident may have had a lower (better) score and ranked $5^{th}$ out of a facility population of 47 residents, but over a period of time (24 hours, a week, a month) has dropped to a ranking of $15^{th}$. Authorized caregivers would be able to drill down into the score and determine what factors may be responsible for the drop in the resident's ranking. From there, it may be left to the staff to determine the cause of the drop in ranking such as fall implications, medication therapy issues, stroke, memory care issues, etc. In this scenario, a resident with a naturally occurring high score might not automatically trigger a cause for concern if their condition has been good and their relative ranking has remained consistent.

In the context of resource allocation, the AAR can be used to "load balance" the residents assigned to caregivers. For example, cumulative scores can be used to determine how residents should be allocated among caregivers such that the workload is evenly distributed. The net result may be that Caregiver A has 10 residents in their care while Caregiver B has 8, but each caregiver has a total combined score for their residents that are comparable. Alternatively, a "hallway" with a higher cumulative score might be allocated an additional caregiver or caregivers based on a documentable higher need as determined by an AAR score.

In an exemplary embodiment, the AAR may be calculated according to the following algorithm:

Resident Home/Away Status:
  Residence occupied=+1 point
Bed Occupancy:
  Less than 7 Hours=+1 point for each 10 minute interval
  More than 10 Hours=+1 point for each 10 minute interval
Out of Bed During Sleeping Hours:
  Each instance=+10 points for each instance
Community Time:
  Less than 4 Hours in Community=+1 point for each 10 minute interval
Fall detection by Logic:
  Each instance=+10 points for each instance
PERS Calls:
  Each instance=+5 points for each instance
MMP:
  Lower Activity Scoring=+1 for each lost point in Activity Score
  Falls Indicated=+10 points for each instance
  Non-Compliance Detected=+1 point for each 10 minute interval
Nighttime Elopement:
  Each instance=+10 points for each instance
Sleep-related Options:
  Change in Bed Time=+X points per 10 minute variation
  Sleep Patterns=−Y points for getting 7-10 hours of sleep
  Change in Arise Time=+X points per 10 minute variation Note that some instances are preceded by other point-generating events which compound the scoring to reflect the severity of the event. i.e. Out of bed during sleeping hours is +10 points, and Fall Detection by Logic (FDL) is +10 points. Both points would be accrued in an FDL event resulting in a total of +20 points. One of skill in the art may appreciate that these factors capture a relatively comprehensive and quantifiable perspective of each resident, wherein the risk that any one factor taken alone may potentially skew the scoring is mitigated by the breadth of the factors taken into account. However, such an array of factors is not intended as limiting on the scope of a system and method as disclosed herein, and any number of equivalent algorithms, combinations or the like may be implemented, either in a rules-based architecture or as part of a machine learning engine, for the implementation of the method described herein.

In one embodiment, and in similar fashion to a fast-tip calculation on a restaurant bill, a fast-staff calculation may generate a display for the total score per caregiver on a shift if there are 4, 5, 6, 7, or 8 on a shift.

One desirable feature of the AAR approach described herein is a "crowd-sourced" relative ranking approach. This crowd-sourced ranking allows each of the residents to serve as a benchmark for the other residents. This methodology allows the identification of macro trends more readily which in some situations will offer some advantages over simply trending a resident's individual AAR score. Rankings can be based on daily, multi-day, weekly or monthly scores. The scores may be averaged as well or limited to certain times (e.g., 6 am to 9 pm each day). Conditions within facilities may tend to vary dramatically from residence layout, to community activities to number of caregivers and acuity of care required by residents. The system may therefore compensate accordingly for embodiments that generate scores and rankings within a single facility, as opposed to those embodiments applying across a number of facilities.

The AAR may enable inter-facility comparisons for the purpose of improving management of facilities. The AAR score can be tied directly or in part to evaluations of a facility's management practices, processes and/or procedures. This may be accomplished via, e.g., raw comparison of scores and/or average scores, a percentage change in scores, changes in the AAR over time, and changes in the AAR in association with landmark changes, for example, changes in management, changes in staff and/or staffing levels, changes in process/procedure/training practices, changes in resident occupancy, etc.

The AAR score may further be used to provide more real-time, empirical management data for determining a facility or facilities' needs for increased services and/or staffing. As such, the AAR score can be used, e.g., to indicate the need of a facility or a group of facilities over another, or to indicate an increased/decreased need at a facility based on changes in AAR.

In one embodiment, the system may further generate an employee care score (ECS) that gives a relative ranking to each caregiver in a facility based on a series of measures captured by the system. Caregivers may be "ranked" on a scale that indicates the relative quality of care provided to the residents. The relative ranking is used for a number of reasons. First, it allows the facility to recognize high and/or low quality performance. Second, it facilitates the appropriate training and/or re-training of staff. Third, it allows the system to identify deviations from process and procedure which may be more or less efficient than current practices. In one example, the best ranking attainable is a score of 1, and the worst possible score can vary and/or be adjusted according to the facility. The ECS may be further refined by combining the ECS with the Auto-Assessment Score associated with a specific resident.

The ECS ranking may improve a facility's quality of care in many ways. For example, the ranking can be used to quantify caregiver performance. Higher scores are indicative of a poor performance. This may or may not include slow response times to calls for assistance, poor adherence to bed check protocols, excessive break periods, social engagement of the patient, late to bed or late to rise issues. The score may be done in aggregate or as an average across the residents in a caregiver's charge, and may be used in performance reviews of caregivers and/or to identify the need for out-of-cycle performance reviews. The score may be used to establish or complement a measure of care level related to billing purposes, to evaluate staffing level needs, and to identify more or less efficient forms of caregiving processes and procedures.

The ECR can be presented in association with a specific resident, either based solely on that resident's calculations or a change in the resident's ECR relative to the ECR for other residents. The score can be used to document quality of care to a resident and/or their family, and/or to address employee performance issues related to a specific resident, such as to identify situations in which equal care is not being provided or to document situations where residents' needs are elevated. The score may be used to identify more or less efficient forms of caregiving processes and procedures.

In various embodiments, the ECR scores and rankings may be used in conjunction with AAR scores and rankings. A high AAR may typically have a direct correlation to a higher ECR, and conversely a low AAR correlates directly to a low ECR. When the AAR is high and ECR is low, the indication would be that there is high quality performance on the part of the caregiver and/or high quality process/procedure. Since the measures are out of synch, this should prompt a review of the employee performance to determine if the loss of correlation is due to deviation from established process/procedure, wherein corrective action may be applied or improvements to process procedure may be discovered, or alternatively to a manipulation of the system itself. When the AAR is low and the ECR is high, the indication would likewise be that there is poor performance on the part of the caregiver and/or poor process/procedure.

In an exemplary embodiment, the AAR may be calculated according to the following algorithm:

Bed Occupancy:
 More than 10 Hours=+1 point for each 10 minute interval

Late Rising:
 Established Waking Time+30 mins=+1 point for each 10 minute interval Late to Bed:
 Established Sleep Time+30 mins=+1 point for each 10 minute interval Community Time:
 Less than 4 Hours AWAY=+1 point for each 10 minute interval Fall detection by Logic:
 Response in <180 seconds=+0 point for each instance
 Response in 181-300 seconds=+1 point for each instance
 Response in 301 seconds=+1 point for each instance
 Each 30 seconds beyond 301=+1 point for each instance PERS Calls:
 Response in <180 seconds=+0 point for each instance
 Response in 181-300 seconds=+1 point for each instance
 Response in 301 seconds=+1 point for each instance
 Each 30 seconds beyond 301=+1 point for each instance MMP:
 Non-Compliance>120 mins Detected=+1 point for each 10 minute interval Bed Check:
 Interval in excess of 120 minutes=+1 point for each 10 minute interval
 No residence entry after door open=+10 points for each instance Other Options:
 Change in Bed Time=+X points per 10 minute variation
 Sleep Patterns=-Y points for getting 7-10 hours of sleep
 Change in Arise Time=+X points per 10 minute variation.

Note that some instances are preceded by other point-generating events which compound the scoring to reflect the severity of the event. For example, "Out of bed during sleeping hours" is +10 points, and "Fall Detection by Logic (FDL)" is +10 points. Both points would be accrued in an FDL event resulting in a total of +20 points.

Like a fast-tip calculation on a restaurant bill, a fast-staff calculation displays the total score per caregiver on a shift if there are 4, 5, 6, 7, or 8 on a shift. The total scores in this manner may be implemented for "load balancing" of caregiver responsibilities and/or resources, wherein for example on any given shift or otherwise periodically a facility may sum the scores for patients assigned to each caregiver and subsequently reallocate room residents to spread the responsibilities more evenly. In accordance with various embodiments as described herein, such reallocation may be facilitated in view of total scores per caregiver, or otherwise for example to ensure a relatively even spread of care scores among each of the caregivers wherein a number of patients with extremely high scores and/or low scores are not assigned to the same caregiver, but rather a relatively equal number of high scores, medium scores and low scores may be allocated to each caregiver accordingly.

A low ECR can be used as a prompt for additional caregiver training. For example, specific instances of poor scores such as slow response to calls or a high number of falls can be used to prompt for more specific training geared towards those specific topics.

Incentives/Gamifying

The method 300 further may include an incentives engine supported by the auto-assessment and employee care scores and rankings as described above. Gaming concepts may be implemented by the system and directed at all levels of the management and staffing, as well as the residents themselves, for the purpose of incentivizing care improvements (step 311).

In one example, management/executive directors may be scored and ranked according to best overall and/or average AAR scores at a single facility or regionally across a plurality of facilities, or according to most improved AAR scores at a single facility or regionally across a plurality of facilities.

In another example, caregivers and/or staff may be scored and ranked according to best overall and/or average AAR scores by resident AAR and/or with respect to all residents assigned to a caregiver, by for example hours of care required for a given score, etc.

In yet another example, competitive scoring may be introduced for residents to encourage resident well-being.

A more simplified look at the AAR may break the AAR scoring up according to the levels at which the scoring was appropriate for review. For example, inter- and intra-facility level AAR scoring may be directed to an audience of management or executive director. Alternatively, individual resident AAR scoring types, whether at the inter- or intra-facility level, may further be directed to caregivers and residents as well.

Event Reporting

The method 300 further may include an event reporting engine which in concert with the scores and rankings as described above may generate graphical user interfaces presenting post-event forensics reports, recommendations and real-time updates according to various embodiments of the present disclosure (step 312).

The post-event forensics reporting module may implement a plain language accounting of an event derived from the data collected in the system. An event in one embodiment may be simply defined as an event requiring assistance, such as a fall or an emergent health event (e.g., stroke, heart attack, medication contraindications, etc.). The event may be one in which a call was made for assistance, or one in which the need was detected by automated methods to determine that assistance may be required. A portion of the forensic reporting feature as disclosed herein may be based in part on the Fall Detection by Logic (FDL) methodology as described above.

Reports may generally be used for internal reporting purposes, for internal filings, as a basis for generating external reports, or for external reporting to family members either at the discretion of the facility or in accordance with regulations (city/state/federal). Family reports may be automatically dispensed, or more likely will require internal review before being sent. Reports may further be used for external purposes for meeting regulatory requirements (city/state/federal) requiring reporting of incidents. The format may be varied to conform to individual reporting requirements.

In one embodiment, a report may be generated in response to a manually-initiated event, such as for example a call for assistance via a push button device such as a Personal Emergency Response System (PERS) device worn on the person, or via a call box as may be mounted in a permanent fashion. The underlined areas in the examples below indicate where the data is pulled from the system and inserted into a plain-language report format, wherein the text in italics indicates text specific to situations where the system is equipped with the ability to provide a "hard clear." It may be understood various highlighting or coloring alternatives to the cited underlining or italics features are within the scope of the present disclosure.

Sample Report 1:

An electronic call for assistance at 4:05:02 PM and issued an alert with a recorded response time of 61 seconds until the residence was known to be accessed via the residence front door at 4:06:03 AM. The call was officially cleared at 4:09:44 PM.

The last verified location of Ms. Smith when the call for assistance came was the bathroom in the residence. Ms. Smith had been in the bathroom for 7 minutes prior to receiving the call for assistance.

Ms. Smith had been in the residence since 3:00:09 PM

During the time between 3:00:09 PM and 4:05:02 PM, Ms. Smith was in the

Bed 45 minutes

Living Room 55 minutes

Bathroom 3 minutes

Bedroom 35 minutes

Upon receiving the electronic call at 4:05:02 AM, the following actions were taken:

An alert text was sent to: 615-555-1212

An alert e-mail was sent to: ed@elf.com

An alert page was sent to: Pager #1027

In one embodiment, a report may be generated in response to an automatically-initiated event, such as for example events detected via the Care Tech FDL algorithm and/or detected via a device using an accelerometer or other automated fall detection technology.

Sample Report 2:

QuietResponse detected a potential fall situation and issued a fall alert at 4:05:02 AM with a recorded response time of 61 seconds until the residence was known to be accessed via the residence front door. The call was officially cleared at 4:09:44 PM.

Ms. Smith had gone to bed at 8:00:09 PM and had gotten out of bed 3 time(s) since then.

At 8:04:33 PM for 1 minute(s)

At 8:23:21 PM for 5 minute(s)

At 3:45:01 AM and did not return

After getting up at 3:45:01 AM, Ms. Smith went from the bedroom to the bathroom to the kitchen.

QuietResponse noted the last activity in the residence at 3:53:04 AM in the kitchen.

At 4:05:02 AM or 20 minutes after leaving the bed and 13 minutes 58 seconds after the last activity was detected, the following actions were taken:

An alert text was sent to: 615-555-1212

An alert e-mail was sent to: ed@elf.com

An alert page was sent to: Pager #1027

The residence door opened indicating a first response at 4:06:03 AM or 61 second after the alert was issued.

In one embodiment, a report may be generated in response to a manually-created event, such as for example an event determined by appropriate staff/caregivers/family to have occurred but not to have generated a call for assistance. These events are manually noted and a "discovery" moment identified. The discovery moment may be tied to a point in time or to a specific data point (i.e. a door open). Events leading up to that point are reconstructed back to a point in time (i.e. 60 minutes prior) and/or to a specific data point (i.e. a previous door close).

Sample Report 3 (sole occupant in residence):

The events between the door closing at 3:09:25 AM and leading up to door opening at 4:59:02 AM have been determined to be of significance.

QuietResponse detected activity as follows:

Residence door closed at 3:09:25 AM

Records indicate activity:

in the kitchen at 3:10:01 AM in the dining room at 3:15:09 AM in the bedroom at 3:15:45 AM Resident was in bed at 3:21:23 AM Resident was out of bed at 4:25:33 AM In the bathroom at 4:26:01 AM Resident was in bed at 4:35:23 AM Resident was out of bed at 4:53:33 AM in the bathroom at 4:54:47 AM Residence door opened at 4:59:02 AM Sample Report 2 (dual occupants in residence):

The events between the door closing at 3:09:25 AM and leading up to door opening at 4:59:02 AM have been determined to be of significance.

QuietResponse detected activity as follows:

Residence door closed at 3:09:25 AM

Quiet Response indicates that the bed was occupied at that time, and there was activity:

in the kitchen at 3:10:01 AM in the dining room at 3:15:09 AM in the bedroom at 3:15:45 AM in the dining room at 3:21:09 AM Residence door opened and closed at 3:21:23 AM and the bed occupied at that time.

Resident was out of bed at 4:25:33 AM

In the bathroom at 4:26:01 AM

Resident was in bed at 4:35:23 AM

Resident was out of bed at 4:53:33 AM in the bathroom at 4:54:47 AM

Residence door opened at 4:59:02 AM

Alternative report format:

The situation with Ms. Smith was discovered at 11:23:45 AM.

Ms. Smith had been in the residence since 10:00:09 AM

During the time between 3:00:09 PM and 4:05:02 PM, Ms. Smith was in the

Bed 45 minutes

Living Room 55 minutes

Bathroom 3 minutes

Bedroom 35 minutes

In one embodiment, a report may include a graphical representation of the data over longer periods that mimic time on a clock, such as for example in a pie chart format.

In a particular embodiment, a resource allocation report according to the present disclosure may implement post-event forensics wherein a graphical log display is generated with one or more primary data points corresponding to an event definition (e.g., wherein the event is confirmed or otherwise manually initiated), and one or more secondary data points retroactively defined as relevant in view of an extrapolated event occurrence (e.g., data points that did not themselves identify an event but are relevant to the subsequent determination of event). The graphical log display may be presented with status indicators over a period of time, such as to highlight in a first manner a range of time between primary data points corresponding to an event period (e.g., from a first positive determination that the subject has fallen to a positive identification that assistance has arrived), and to highlight in a second manner a range of time between secondary and primary points on either end of the event period (e.g., a time during which the subject had fallen but the fall was not yet determined).

A system according to the present disclosure may generate and implement a user interface accessible via a communications network by remote users such as for example caregivers. An exemplary Web-Based version of the Caregiver Interface 900 as represented in FIG. 9 may be designed to provide the caregiver(s) with an easily interpreted view of the data and function within the Smart Remote Monitoring System. Basic patient information appears in the top right quadrant of the Dashboard tab. This area displays the patient's name and other core information is displayed to confirm that the patient is the one associated with the caregiver. Recent Activity appears below that in the bottom right quadrant. This section displays some of the aggregated and derivative data from the system including but not limited to distribution of time spent in a given area, number of exterior/refrigerator/pantry door opens, trends in those distributions (time to bed, hours slept, door opens by day, etc.). Alerts, in the bottom left quadrant, are alerts presented in a color-coded system indicating whether those alerts are of low, moderate or high priority. These are system-generated alerts stemming from the fall detection by logic algorithm, late to bed, late to rise, and other system alerts as well as PERS activation alerts. Care Notes in the top left corner of the Dashboard tab shows the integration of social media with the Smart Remote Monitoring System. Alerts are also incorporated into the Care Notes to provide a comprehensive record of the patient's daily activities.

Figure 10:
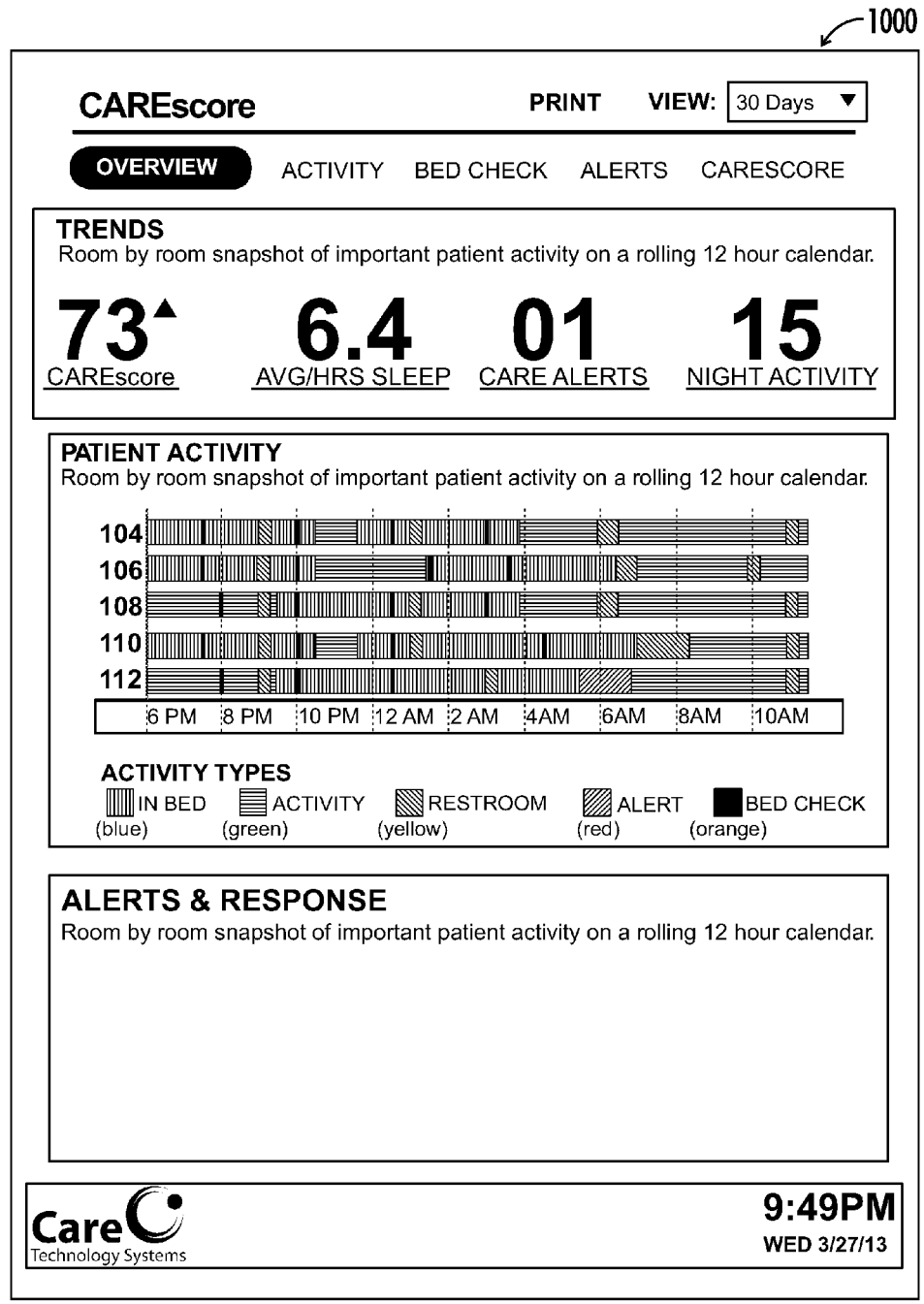
FIG. 10 is an image representing a screen shot from another exemplary user interface generated by a system according to the present disclosure.

Another exemplary user interface display 1000 as represented in FIG. 10 may present an individual or room-by-room "snapshot" of relevant patient activity or events along a sliding graph, for example as may correspond to a user-selectable time frame.

Figure 11:
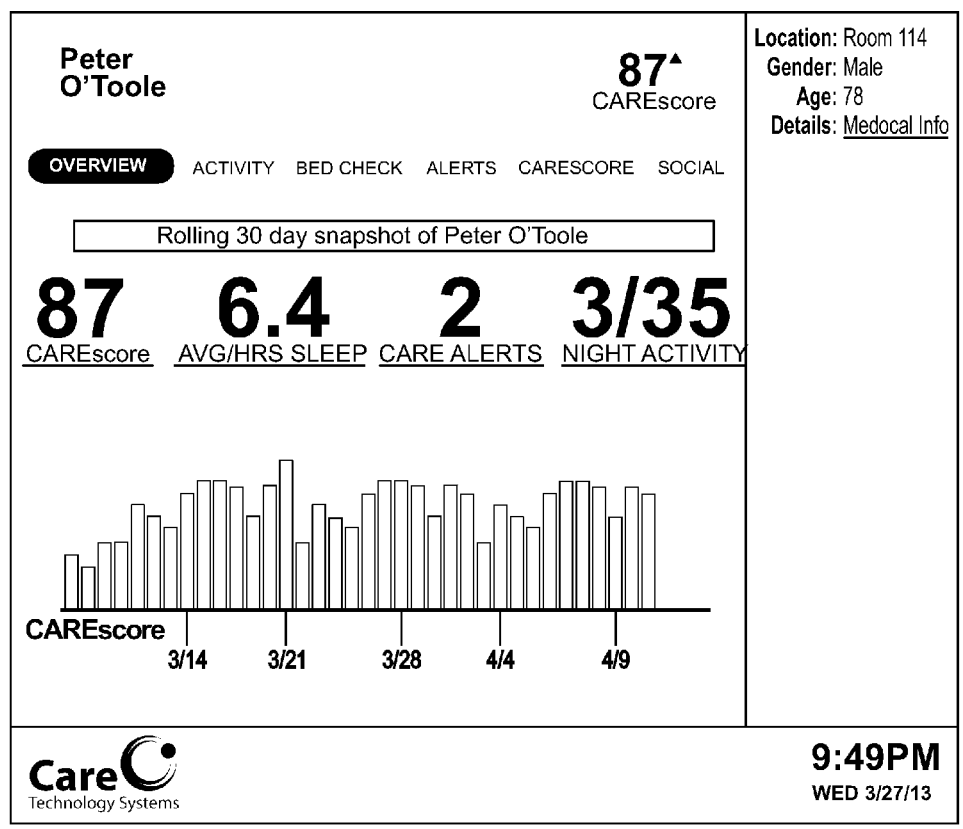
FIG. 11 is an image representing a screen shot from another user interface generated by a system according to the present disclosure.

Yet another exemplary user interface display 1100 as represented in FIG. 11 may present a rolling snapshot of AAR scores or other relevant data as a bar graph for more direct comparison with respect to time.

The previous detailed description has been provided for the purposes of illustration and description. Thus, although there have been described particular embodiments of a System and Method of Automated Healthcare Assessments and Event Inferences, it is not intended that such references be construed as limitations upon the scope of an invention as disclosed herein except as set forth in the following claims.

What is claimed is:

1. A healthcare assessment system comprising:
  a plurality of defined areas in a healthcare facility, each area associated with a healthcare subject and further comprising a first set of one or more sensors effective to generate output signals representative of biometric data for the subject, and a second set of one or more sensors effective to generate output signals representative of activity within the area;
  a server functionally linked via a communications network to the first set of one or more sensors and the second set of one or more sensors and further comprising a data processor, a data storage network and a non-transitory computer-readable medium having program instructions residing thereon, the instructions executable by the processor to direct the performance of operations further comprising:
    storing biometric and activity data points for each subject in the data storage network, the biometric and activity data points based at least in part on inputs from the first set of one or more sensors and the second set of one or more sensors,
    determining potential events relevant to each subject for system monitoring based on a respective healthcare profile,
    executing an event inference engine identifying actual occurrence of one or more of the potential events based on one or more stored data points with respect to time,
    for identified actual occurrences of an event, post-event monitoring of activity data to determine a severity of the respective event,
    aggregating data comprising actual events, determined severity of the actual events, and associated data points in the data storage network,
    reverse analyzing post-event data points and pre-event data points represented by the aggregated data for extrapolating a likely occurrence of such events and a likely severity of such events for a respective subject,
    assigning values representative of a level of healthcare resource needs for each subject, the values determined based on respective healthcare profiles and the identified and extrapolated events, and
    delivering an intervention prompt to a graphical user interface on a display unit of a user computing device for a healthcare provider associated with the respective subject, wherein the intervention prompt is prioritized based on a relative post-event activity level of the subject with respect to a pre-event activity level, and
  the user interface comprising a resource allocation report with relative rankings of the assigned values for each subject associated with the healthcare facility.

2. The system of claim 1, the operation of extrapolating likely occurrence of potential events further comprising matching an identified combination of data points with a predetermined combination of data points representative of an event relevant to a high-risk condition associated with the respective subject.

3. The system of claim 1, the instructions further executable to direct the performance of an operation of categorizing the identified or extrapolated events as billable events with respect to a particular subject.

4. The system of claim 3, the instructions further executable to direct the performance of an operation of cross-checking the categorized billable events against a list of actual billed events with respect to the subject.

5. The system of claim 4, the instructions further executable to direct the performance of an operation of generating a second user interface effective to enable user confirmation of one or more categorized billable events with respect to the subject.

6. The system of claim 1, the resource allocation report further comprising a graphical event log display with one or more primary data points corresponding to an event definition, and one or more secondary data points retroactively defined as relevant in view of an extrapolated event occurrence.

7. The system of claim 6, the graphical event log display further comprising a first highlighted time range between at least first and second primary data points corresponding to an event period, and one or more separately highlighted time ranges between secondary and a primary data points on either end of the event period.

8. A healthcare assessment system comprising:
a plurality of defined areas in a healthcare facility comprising a plurality of healthcare providers, each area associated with a healthcare subject and further comprising a first set of one or more sensors effective to generate output signals representative of biometric data for the subject, and a second set of one or more sensors effective to generate output signals representative of activity within the area;
a server functionally linked via a communications network to the first set of one or more sensors and the second set of one or more sensors and further comprising a data processor, a data storage network and a non-transitory computer-readable medium having program instructions residing thereon, the instructions executable by the processor to direct the performance of operations further comprising:
storing biometric and activity data points for each subject in the data storage network, the biometric and activity data points based at least in part on inputs from the first set of one or more sensors and the second set of one or more sensors,
determining potential events relevant to each subject for system monitoring based on a respective healthcare profile,
executing an event inference engine identifying actual occurrence of one or more of the potential events based on one or more stored data points with respect to time,
identifying one or more healthcare providers associated with each identified event,
for identified actual occurrences of an event, post-event monitoring of activity data to determine a severity of the respective event,
aggregating data comprising actual events, associated healthcare providers, determined severity of the actual events, and associated data points in the data storage network,
reverse analyzing post-event data points and pre-event data points represented by the aggregated data for extrapolating a likely occurrence of such events and a likely severity of such events for a respective subject,
delivering an intervention prompt to a graphical user interface on a display unit of one or more user computing devices for the healthcare providers associated with the respective subject, wherein the intervention prompt is prioritized based on a relative post-event activity level of the subject with respect to a pre-event activity level,
assigning values representative of a level of healthcare resource needs for each subject, the values determined based on respective healthcare profiles and the identified and extrapolated events,
assigning values representative of a quality of healthcare resources provided for each healthcare provider, the values determined based on the assigned values for relevant subjects and the identified events and intervention prompts associated with the respective provider, and
generating a resource allocation report with relative rankings of the assigned values for each subject and for each provider associated with the healthcare facility.

9. The system of claim 8, the operation of extrapolating likely occurrence of potential events further comprising matching an identified combination of data points with a predetermined combination of data points representative of an event relevant to a high-risk condition associated with the respective subject.

10. The system of claim 8, the instructions further executable to direct the performance of an operation of categorizing the identified or extrapolated events as billable events with respect to a particular subject and a particular healthcare provider.

11. The system of claim 10, the instructions further executable to direct the performance of an operation of cross-checking the categorized billable events against a list of actual billed events with respect to the subject.

12. The system of claim 11, the instructions further executable to direct the performance of an operation of generating a second user interface effective to enable user confirmation of one or more categorized billable events with respect to the subject.

13. The system of claim 8, the resource allocation report further comprising a graphical event log display with one or more primary data points corresponding to an event definition, and one or more secondary data points retroactively defined as relevant in view of an extrapolated event occurrence.

14. The system of claim 13, the graphical event log display further comprising a first highlighted time range between at least first and second primary data points corresponding to an event period, and one or more separately highlighted time ranges between secondary and a primary data points on either end of the event period.

15. A healthcare assessment system comprising:
a plurality of healthcare facilities each comprising a plurality of healthcare providers and a plurality of defined areas, each area associated with a healthcare subject and further comprising a first set of one or more sensors effective to generate output signals representative of biometric data for the subject, and a second set of one or more sensors effective to generate output signals representative of activity within the area;
a server functionally linked via a communications network to the first set of one or more sensors and the second set of one or more sensors and further comprising a data processor, a data storage network and a non-transitory computer-readable medium having program instructions residing thereon, the instructions executable by the processor to direct the performance of operations further comprising:
storing biometric and activity data points for each subject in the data storage network, the biometric and activity data points based at least in part on inputs from the first set of one or more sensors and the second set of one or more sensors,
determining potential events relevant to each subject for system monitoring based on a respective healthcare profile,
executing an event inference engine identifying actual occurrence of one or more of the potential events based on one or more stored data points with respect to time,
identifying one or more healthcare providers associated with each identified event,
for identified actual occurrences of an event, post-event monitoring of activity data to determine a severity of the respective event,
aggregating data comprising actual events, determined severity of the actual events, and associated data points in the data storage network, reverse analyzing post-event data points and pre-event data points represented by the aggregated data for extrapolating a likely occurrence of such events and a likely severity of such events for a respective subject, delivering an intervention prompt to a graphical user interface on a display unit of one or more user computing devices for the healthcare providers associated with the respective subject, wherein the intervention prompt is prioritized based on a relative post-event activity level of the subject with respect to a pre-event activity level, assigning values representative of a level of healthcare resource needs for each subject, the values determined based on respective healthcare profiles and the identified and extrapolated events, assigning values representative of a quality of healthcare resources provided for each healthcare provider, the values determined based on the assigned values for relevant subjects and the identified events and intervention prompts associated with the respective provider, and generating a resource allocation report with user-selectable lists of relative rankings of the assigned values for each subject associated with a healthcare facility, each provider associated with a healthcare facility, and for each healthcare facility with respect to the plurality of facilities.

16. The system of claim 15, further comprising means for categorizing the identified or extrapolated events as billable events with respect to a particular subject and a particular healthcare provider.

17. The system of claim 16, further comprising means for cross-checking the categorized billable events against a list of actual billed events with respect to the subject.

18. The system of claim 17, further comprising means for enabling user confirmation of one or more categorized billable events with respect to the subject.

19. The system of claim 15, the resource allocation report further comprising a graphical event log display with one or more primary data points corresponding to an event definition, and one or more secondary data points retroactively defined as relevant in view of an extrapolated event occurrence, the graphical event log display further comprising a first highlighted time range between at least first and second primary data points corresponding to an event period, and one or more separately highlighted time ranges between secondary and a primary data points on either end of the event period.

* * * * *